(12) United States Patent
Long

(10) Patent No.: US 7,655,004 B2
(45) Date of Patent: Feb. 2, 2010

(54) ELECTROPORATION ABLATION APPARATUS, SYSTEM, AND METHOD

(75) Inventor: Gary L. Long, Cincinnati, OH (US)

(73) Assignee: Ethicon Endo-Surgery, Inc., Cincinnati, OH (US)

(*) Notice: Subject to any disclaimer, the term of this patent is extended or adjusted under 35 U.S.C. 154(b) by 202 days.

(21) Appl. No.: 11/706,766

(22) Filed: Feb. 15, 2007

(65) Prior Publication Data

US 2008/0200912 A1    Aug. 21, 2008

(51) Int. Cl.
*A61B 18/04*    (2006.01)
*A61B 1/00*    (2006.01)
(52) U.S. Cl. ......................... 606/37; 600/103
(58) Field of Classification Search .............. 600/101, 600/104, 153, 160, 106, 137; 606/32–50; 607/96–100
See application file for complete search history.

(56) References Cited

U.S. PATENT DOCUMENTS

| | | |
|---|---|---|
| 1,127,948 A | 2/1915 | Wappler |
| 2,028,635 A | 1/1936 | Wappler |
| 2,113,246 A | 4/1938 | Wappler |
| 3,470,876 A | 10/1969 | Barchilon |
| 3,994,301 A | 11/1976 | Agris |
| 4,178,920 A | 12/1979 | Cawood, Jr. et al. |
| 4,207,873 A | 6/1980 | Kruy |
| 4,235,238 A | 11/1980 | Ogiu et al. |
| 4,258,716 A | 3/1981 | Sutherland |
| 4,278,077 A | 7/1981 | Mizumoto |
| 4,285,344 A | 8/1981 | Marshall |
| 4,396,021 A | 8/1983 | Baumgartner |
| 4,452,246 A | 6/1984 | Bader et al. |
| 4,461,281 A | 7/1984 | Carson |
| 4,491,132 A | 1/1985 | Aikins |

(Continued)

FOREIGN PATENT DOCUMENTS

DE    19757056 B4    8/2008

(Continued)

OTHER PUBLICATIONS

Edd, et al., "In Vivo Results of a New Focal Tissue Ablation Technique: Irreversible Electroporation," IEEE Trans Biomed Eng, vol, 53, pp. 1409-1415, 2006.

(Continued)

*Primary Examiner*—Michael Peffley
*Assistant Examiner*—Ronald J Hupczey, Jr.

(57) ABSTRACT

A surgical instrument, such as an endoscopic or laparoscopic instrument, includes an ablation device. The ablation device includes an elongate flexible member having a proximal end and a distal end. A first working channel is formed within the flexible member. A first diagnostic probe having a proximal end and distal end is located within the first working channel and extends through the distal end of the flexible member. A first electrode is connected to the distal end of the first diagnostic probe electrode is adapted to be endoscopically located in a tissue treatment region. The first electrode is adapted to couple to an electrical waveform generator to receive an irreversible electroporation electrical waveform sufficient to ablate tissue located proximate to the first electrode. A system further includes an electrical waveform generator electrically coupled to the first electrode of the ablation device to generate an IRE waveform sufficient to ablate tissue located proximate to the first electrode.

12 Claims, 12 Drawing Sheets

U.S. PATENT DOCUMENTS

| | | |
|---|---|---|
| 4,527,331 A | 7/1985 | Lasner et al. |
| 4,538,594 A | 9/1985 | Boebel et al. |
| D281,104 S | 10/1985 | Davison |
| 4,580,551 A | 4/1986 | Siegmund et al. |
| 4,646,722 A | 3/1987 | Silverstein et al. |
| 4,653,476 A | 3/1987 | Bonnet |
| 4,669,470 A | 6/1987 | Brandfield |
| 4,685,447 A | 8/1987 | Iversen et al. |
| 4,711,240 A | 12/1987 | Goldwasser et al. |
| 4,712,545 A | 12/1987 | Honkanen |
| D295,894 S | 5/1988 | Sharkany et al. |
| 4,763,669 A | 8/1988 | Jaeger |
| 4,873,979 A | 10/1989 | Hanna |
| 4,880,015 A | 11/1989 | Nierman |
| 4,911,148 A | 3/1990 | Sosnowski et al. |
| 4,926,860 A | 5/1990 | Stice et al. |
| 4,938,214 A | 7/1990 | Specht et al. |
| 4,950,273 A | 8/1990 | Briggs |
| 4,984,581 A | 1/1991 | Stice |
| 5,020,514 A | 6/1991 | Heckele |
| 5,020,535 A | 6/1991 | Parker et al. |
| 5,025,778 A | 6/1991 | Silverstein et al. |
| 5,037,433 A | 8/1991 | Wilk et al. |
| 5,041,129 A | 8/1991 | Hayhurst et al. |
| 5,046,513 A | 9/1991 | Gatturna et al. |
| 5,050,585 A | 9/1991 | Takahashi |
| 5,065,516 A | 11/1991 | Dulebohn |
| 5,066,295 A | 11/1991 | Kozak et al. |
| 5,123,914 A | 6/1992 | Cope |
| 5,133,727 A | 7/1992 | Bales et al. |
| 5,174,300 A | 12/1992 | Bales et al. |
| 5,176,126 A | 1/1993 | Chikama |
| 5,192,284 A | 3/1993 | Pleatman |
| 5,201,752 A | 4/1993 | Brown et al. |
| 5,201,908 A | 4/1993 | Jones |
| 5,203,785 A | 4/1993 | Slater |
| 5,203,787 A | 4/1993 | Noblitt et al. |
| 5,209,747 A | 5/1993 | Knoepfler |
| 5,219,357 A | 6/1993 | Honkanen et al. |
| 5,219,358 A | 6/1993 | Bendel et al. |
| 5,234,453 A | 8/1993 | Smith et al. |
| 5,235,964 A | 8/1993 | Abenaim |
| 5,246,424 A | 9/1993 | Wilk |
| 5,259,366 A | 11/1993 | Reydel et al. |
| 5,263,958 A | 11/1993 | deGuillebon et al. |
| 5,273,524 A | 12/1993 | Fox et al. |
| 5,275,607 A | 1/1994 | Lo et al. |
| 5,284,128 A | 2/1994 | Hart |
| 5,290,302 A | 3/1994 | Pericic |
| 5,295,977 A | 3/1994 | Cohen et al. |
| 5,297,536 A | 3/1994 | Wilk |
| 5,312,416 A | 5/1994 | Spaeth et al. |
| 5,320,636 A | 6/1994 | Slater |
| 5,325,845 A | 7/1994 | Adair |
| 5,330,471 A | 7/1994 | Eggers |
| 5,330,496 A | 7/1994 | Alferness |
| 5,330,502 A | 7/1994 | Hassler et al. |
| 5,331,971 A | 7/1994 | Bales et al. |
| 5,334,198 A | 8/1994 | Hart et al. |
| 5,344,428 A | 9/1994 | Griffiths |
| 5,350,391 A | 9/1994 | Iacovelli |
| 5,352,184 A | 10/1994 | Goldberg et al. |
| 5,352,222 A | 10/1994 | Rydell |
| 5,354,311 A | 10/1994 | Kambin et al. |
| 5,356,408 A | 10/1994 | Rydell |
| 5,364,410 A | 11/1994 | Failla et al. |
| 5,366,466 A | 11/1994 | Christian et al. |
| 5,366,467 A | 11/1994 | Lynch et al. |
| 5,368,605 A | 11/1994 | Miller, Jr. |
| 5,383,877 A | 1/1995 | Clarke |
| 5,383,888 A | 1/1995 | Zvenyatsky et al. |
| 5,392,789 A | 2/1995 | Slater et al. |
| 5,395,386 A | 3/1995 | Slater |
| 5,401,248 A | 3/1995 | Bencini |
| 5,403,342 A | 4/1995 | Tovey et al. |
| 5,403,348 A | 4/1995 | Bonutti |
| 5,405,359 A | 4/1995 | Pierce |
| 5,433,721 A | 7/1995 | Hooven et al. |
| 5,439,471 A | 8/1995 | Kerr |
| 5,439,478 A | 8/1995 | Palmer |
| 5,441,059 A | 8/1995 | Dannan |
| 5,449,021 A | 9/1995 | Chikama |
| 5,456,684 A | 10/1995 | Schmidt et al. |
| 5,458,131 A | 10/1995 | Wilk |
| 5,458,583 A | 10/1995 | McNeely et al. |
| 5,460,168 A | 10/1995 | Masubuchi et al. |
| 5,465,731 A | 11/1995 | Bell et al. |
| 5,467,763 A | 11/1995 | McMahon et al. |
| 5,468,250 A | 11/1995 | Paraschac et al. |
| 5,470,308 A * | 11/1995 | Edwards et al. ............... 604/22 |
| 5,470,320 A | 11/1995 | Tiefenbrun et al. |
| 5,478,347 A | 12/1995 | Aranyi |
| 5,480,404 A | 1/1996 | Kammerer et al. |
| 5,482,054 A | 1/1996 | Slater et al. |
| 5,484,451 A | 1/1996 | Akopov et al. |
| 5,489,256 A | 2/1996 | Adair |
| 5,496,347 A | 3/1996 | Hashiguchi et al. |
| 5,499,992 A | 3/1996 | Meade et al. |
| 5,503,616 A | 4/1996 | Jones |
| 5,505,686 A | 4/1996 | Willis et al. |
| 5,511,564 A | 4/1996 | Wilk |
| 5,514,157 A | 5/1996 | Nicholas et al. |
| 5,522,829 A | 6/1996 | Michalos |
| 5,522,830 A | 6/1996 | Aranyi |
| 5,554,151 A | 9/1996 | Hinchliffe |
| 5,562,693 A | 10/1996 | Devlin et al. |
| 5,569,243 A | 10/1996 | Kortenbach et al. |
| 5,569,298 A | 10/1996 | Schnell |
| 5,578,030 A * | 11/1996 | Levin ........................ 606/39 |
| 5,584,845 A | 12/1996 | Hart |
| 5,593,420 A | 1/1997 | Eubanks, Jr et al. |
| 5,595,562 A | 1/1997 | Grier |
| 5,597,378 A | 1/1997 | Jervis |
| 5,601,573 A | 2/1997 | Fogelberg et al. |
| 5,601,588 A | 2/1997 | Tonomura et al. |
| 5,604,531 A | 2/1997 | Iddan et al. |
| 5,607,389 A * | 3/1997 | Edwards et al. ............... 604/22 |
| 5,607,450 A | 3/1997 | Zvenyatsky et al. |
| 5,618,303 A | 4/1997 | Marlow et al. |
| 5,624,399 A | 4/1997 | Ackerman |
| 5,628,732 A | 5/1997 | Antoon, Jr. et al. |
| 5,630,782 A | 5/1997 | Adair |
| 5,643,294 A | 7/1997 | Tovey et al. |
| 5,649,372 A | 7/1997 | Souza |
| 5,653,677 A | 8/1997 | Okada et al. |
| 5,662,663 A | 9/1997 | Shallman |
| 5,669,875 A | 9/1997 | van Eerdenburg |
| 5,681,324 A | 10/1997 | Kammerer et al. |
| 5,681,330 A | 10/1997 | Hughett et al. |
| 5,685,820 A | 11/1997 | Riek et al. |
| 5,695,448 A | 12/1997 | Kimura et al. |
| 5,695,511 A | 12/1997 | Cano et al. |
| 5,730,740 A | 3/1998 | Wales et al. |
| 5,741,278 A | 4/1998 | Stevens |
| 5,741,285 A | 4/1998 | McBrayer et al. |
| 5,746,759 A | 5/1998 | Meade et al. |
| 5,749,889 A | 5/1998 | Bacich et al. |
| 5,752,951 A | 5/1998 | Yanik |
| 5,766,167 A | 6/1998 | Eggers et al. |
| 5,766,170 A | 6/1998 | Eggers |
| 5,766,205 A | 6/1998 | Zvenyatsky et al. |
| 5,769,849 A | 6/1998 | Eggers |
| 5,779,701 A | 7/1998 | McBrayer et al. |
| 5,779,716 A | 7/1998 | Cano et al. |

| | | | | | | |
|---|---|---|---|---|---|---|
| 5,779,727 | A | 7/1998 | Orejola | 6,206,872 B1 | 3/2001 | Lafond et al. |
| 5,792,113 | A | 8/1998 | Kramer et al. | 6,206,877 B1 | 3/2001 | Kese et al. |
| 5,792,153 | A | 8/1998 | Swain et al. | 6,261,242 B1 * | 7/2001 | Roberts et al. ............... 600/564 |
| 5,792,165 | A | 8/1998 | Klieman et al. | 6,264,664 B1 | 7/2001 | Avellanet |
| 5,797,835 | A | 8/1998 | Green | 6,277,136 B1 | 8/2001 | Bonutti |
| 5,797,939 | A | 8/1998 | Yoon | 6,283,963 B1 | 9/2001 | Regula |
| 5,797,941 | A | 8/1998 | Schulze et al. | 6,293,909 B1 | 9/2001 | Chu et al. |
| 5,803,903 | A | 9/1998 | Athas et al. | 6,293,952 B1 | 9/2001 | Brosens et al. |
| 5,808,665 | A | 9/1998 | Green | 6,322,578 B1 | 11/2001 | Houle et al. |
| 5,810,806 | A | 9/1998 | Ritchart et al. | 6,326,177 B1 | 12/2001 | Schoenbach et al. |
| 5,810,865 | A | 9/1998 | Koscher et al. | 6,350,267 B1 | 2/2002 | Stefanchik |
| 5,810,876 | A | 9/1998 | Kelleher | 6,352,503 B1 | 3/2002 | Matsui et al. |
| 5,810,877 | A | 9/1998 | Roth et al. | 6,355,035 B1 | 3/2002 | Manushakian |
| 5,813,976 | A | 9/1998 | Filipi et al. | 6,371,956 B1 | 4/2002 | Wilson et al. |
| 5,814,058 | A | 9/1998 | Carlson et al. | 6,379,366 B1 | 4/2002 | Fleischman et al. |
| 5,817,061 | A | 10/1998 | Goodwin et al. | 6,383,197 B1 | 5/2002 | Conlon et al. |
| 5,817,119 | A | 10/1998 | Klieman et al. | 6,391,029 B1 | 5/2002 | Hooven et al. |
| 5,819,736 | A | 10/1998 | Avny et al. | 6,406,440 B1 | 6/2002 | Stefanchik |
| 5,827,281 | A | 10/1998 | Levin | 6,409,733 B1 | 6/2002 | Conlon et al. |
| 5,830,231 | A | 11/1998 | Geiges, Jr. | 6,447,511 B1 | 9/2002 | Slater |
| 5,833,700 | A | 11/1998 | Fogelberg et al. | 6,447,523 B1 | 9/2002 | Middleman et al. |
| 5,833,703 | A | 11/1998 | Manushakian | 6,454,783 B1 | 9/2002 | Piskun |
| 5,843,017 | A | 12/1998 | Yoon | 6,454,785 B2 | 9/2002 | De Hoyos Garza |
| 5,849,022 | A | 12/1998 | Sakashita et al. | 6,464,701 B1 | 10/2002 | Hooven et al. |
| 5,860,913 | A | 1/1999 | Yamaya et al. | 6,475,104 B1 | 11/2002 | Lutz et al. |
| 5,860,995 | A | 1/1999 | Berkelaar | 6,485,411 B1 | 11/2002 | Konstorum et al. |
| 5,882,331 | A | 3/1999 | Sasaki | 6,491,626 B1 | 12/2002 | Stone et al. |
| 5,882,344 | A | 3/1999 | Stouder, Jr. | 6,494,893 B2 | 12/2002 | Dubrul et al. |
| 5,893,846 | A | 4/1999 | Bales et al. | 6,503,192 B1 | 1/2003 | Ouchi |
| 5,893,874 | A | 4/1999 | Bourque et al. | 6,506,190 B1 | 1/2003 | Walshe |
| 5,893,875 | A | 4/1999 | O'Connor et al. | 6,508,827 B1 | 1/2003 | Manhes |
| 5,899,919 | A | 5/1999 | Eubanks, Jr. et al. | 6,543,456 B1 | 4/2003 | Freeman |
| 5,908,420 | A | 6/1999 | Parins et al. | 6,551,270 B1 | 4/2003 | Bimbo et al. |
| 5,916,147 | A | 6/1999 | Boury | 6,558,384 B2 | 5/2003 | Mayenberger |
| 5,921,997 | A | 7/1999 | Fogelberg et al. | 6,562,035 B1 | 5/2003 | Levin |
| 5,922,008 | A | 7/1999 | Gimpelson | 6,569,159 B1 | 5/2003 | Edwards et al. |
| 5,925,052 | A | 7/1999 | Simmons | 6,572,629 B1 | 6/2003 | Kalloo et al. |
| 5,928,255 | A | 7/1999 | Meade et al. | 6,572,635 B1 | 6/2003 | Bonutti |
| 5,944,718 | A | 8/1999 | Austin et al. | 6,575,988 B2 | 6/2003 | Rousseau |
| 5,951,549 | A | 9/1999 | Richardson et al. | 6,592,559 B1 | 7/2003 | Pakter et al. |
| 5,954,720 | A | 9/1999 | Wilson et al. | 6,592,603 B2 | 7/2003 | Lasner |
| 5,954,731 | A * | 9/1999 | Yoon ........................ 606/144 | 6,605,105 B1 | 8/2003 | Cuschieri et al. |
| 5,957,943 | A | 9/1999 | Vaitekunas | 6,652,521 B2 | 11/2003 | Schulze |
| 5,957,953 | A | 9/1999 | DiPoto et al. | 6,652,551 B1 | 11/2003 | Heiss |
| 5,971,995 | A | 10/1999 | Rousseau | 6,663,641 B1 | 12/2003 | Kovac et al. |
| 5,976,075 | A | 11/1999 | Beane et al. | 6,672,338 B1 | 1/2004 | Esashi et al. |
| 5,976,130 | A | 11/1999 | McBrayer et al. | 6,673,087 B1 | 1/2004 | Chang et al. |
| 5,980,556 | A | 11/1999 | Giordano et al. | 6,685,628 B2 | 2/2004 | Vu |
| 5,984,938 | A | 11/1999 | Yoon | 6,692,445 B2 * | 2/2004 | Roberts et al. ............... 600/564 |
| 5,989,182 | A | 11/1999 | Hori et al. | 6,692,462 B2 | 2/2004 | Mackenzie et al. |
| 5,993,447 | A * | 11/1999 | Blewett et al. ................ 606/50 | 6,699,180 B2 | 3/2004 | Kobayashi |
| 6,001,120 | A | 12/1999 | Levin | 6,699,256 B1 | 3/2004 | Logan et al. |
| 6,004,330 | A | 12/1999 | Middleman et al. | 6,699,263 B2 | 3/2004 | Cope |
| 6,010,515 | A | 1/2000 | Swain et al. | 6,716,226 B2 | 4/2004 | Sixto, Jr. et al. |
| 6,019,770 | A | 2/2000 | Christoudias | 6,740,030 B2 | 5/2004 | Martone et al. |
| 6,024,708 | A | 2/2000 | Bales et al. | 6,743,240 B2 | 6/2004 | Smith et al. |
| 6,027,522 | A | 2/2000 | Palmer | 6,749,560 B1 | 6/2004 | Konstorum et al. |
| 6,030,365 | A | 2/2000 | Laufer | 6,749,609 B1 | 6/2004 | Lunsford et al. |
| 6,033,399 | A | 3/2000 | Gines | 6,752,811 B2 | 6/2004 | Chu et al. |
| 6,053,927 | A | 4/2000 | Hamas | 6,761,685 B2 | 7/2004 | Adams et al. |
| 6,068,629 | A | 5/2000 | Haissaguerre et al. | 6,773,434 B2 | 8/2004 | Ciarrocca |
| 6,071,233 | A | 6/2000 | Ishikawa et al. | 6,780,151 B2 | 8/2004 | Grabover et al. |
| 6,090,108 | A | 7/2000 | McBrayer et al. | 6,780,352 B2 | 8/2004 | Jacobson |
| 6,096,046 | A | 8/2000 | Weiss | 6,783,491 B2 | 8/2004 | Saadat et al. |
| 6,110,183 | A | 8/2000 | Cope | 6,786,864 B2 | 9/2004 | Matsuura et al. |
| 6,139,555 | A | 10/2000 | Hart et al. | 6,790,173 B2 | 9/2004 | Saadat et al. |
| 6,149,662 | A | 11/2000 | Pugliesi et al. | 6,800,056 B2 | 10/2004 | Tartaglia et al. |
| 6,159,200 | A | 12/2000 | Verdura et al. | 6,808,491 B2 | 10/2004 | Kortenbach et al. |
| 6,165,184 | A | 12/2000 | Verdura et al. | 6,824,548 B2 | 11/2004 | Smith et al. |
| 6,168,605 | B1 | 1/2001 | Measamer et al. | 6,837,847 B2 | 1/2005 | Ewers et al. |
| 6,179,776 | B1 | 1/2001 | Adams et al. | 6,843,794 B2 | 1/2005 | Sixto, Jr. et al. |
| 6,179,837 | B1 | 1/2001 | Hooven | 6,861,250 B1 | 3/2005 | Cole et al. |
| 6,203,533 | B1 | 3/2001 | Ouchi | 6,878,110 B2 | 4/2005 | Yang et al. |

| | | | | | |
|---|---|---|---|---|---|
| 6,884,213 B2 | 4/2005 | Raz et al. | 7,422,590 B2 | 9/2008 | Kupferschmid et al. |
| 6,887,255 B2 | 5/2005 | Shimm | 7,497,867 B2 | 3/2009 | Lasner et al. |
| 6,896,683 B1 | 5/2005 | Gadberry et al. | 7,544,203 B2 | 6/2009 | Chin et al. |
| 6,908,476 B2 | 6/2005 | Jud et al. | 2001/0049497 A1 | 12/2001 | Kalloo et al. |
| 6,918,871 B2 | 7/2005 | Schulze | 2002/0022857 A1 | 2/2002 | Goldsteen et al. |
| 6,932,810 B2 | 8/2005 | Ryan | 2002/0023353 A1 | 2/2002 | Ting-Kung |
| 6,932,827 B2 | 8/2005 | Cole | 2002/0068945 A1 | 6/2002 | Sixto, Jr. et al. |
| 6,942,613 B2 | 9/2005 | Ewers et al. | 2002/0078967 A1 | 6/2002 | Sixto, Jr. et al. |
| 6,945,979 B2 | 9/2005 | Kortenbach et al. | 2002/0082516 A1 | 6/2002 | Stefanchik |
| 6,958,035 B2 | 10/2005 | Friedman et al. | 2002/0091391 A1 | 7/2002 | Cole et al. |
| 6,960,162 B2 | 11/2005 | Saadat et al. | 2002/0107530 A1 | 8/2002 | Sauer et al. |
| 6,960,163 B2 | 11/2005 | Ewers et al. | 2002/0138086 A1 | 9/2002 | Sixto, Jr. et al. |
| 6,962,587 B2 | 11/2005 | Johnson et al. | 2002/0147456 A1 | 10/2002 | Diduch et al. |
| 6,964,662 B2 | 11/2005 | Kidooka | 2002/0183591 A1 | 12/2002 | Matsuura et al. |
| 6,966,909 B2 | 11/2005 | Marshall et al. | 2003/0036679 A1 | 2/2003 | Kortenbach et al. |
| 6,967,462 B1 | 11/2005 | Landis | 2003/0114732 A1 | 6/2003 | Webler et al. |
| 6,971,988 B2 | 12/2005 | Orban, III | 2003/0130564 A1 | 7/2003 | Martone et al. |
| 6,972,017 B2 | 12/2005 | Smith et al. | 2003/0130656 A1 | 7/2003 | Levin |
| 6,976,992 B2 | 12/2005 | Sachatello et al. | 2003/0171651 A1 | 9/2003 | Page et al. |
| 6,984,205 B2 | 1/2006 | Gazdzinski | 2003/0176880 A1 | 9/2003 | Long et al. |
| 6,988,987 B2 | 1/2006 | Ishikawa et al. | 2003/0191497 A1 | 10/2003 | Cope |
| 6,991,627 B2 | 1/2006 | Madhani et al. | 2003/0195565 A1 | 10/2003 | Bonutti |
| 6,994,708 B2 | 2/2006 | Manzo | 2003/0216611 A1 | 11/2003 | Vu |
| 6,997,931 B2 | 2/2006 | Sauer et al. | 2003/0216615 A1 | 11/2003 | Ouchi |
| 7,008,375 B2 | 3/2006 | Weisel | 2003/0225312 A1 | 12/2003 | Suzuki et al. |
| 7,009,634 B2 | 3/2006 | Iddan et al. | 2003/0229269 A1 | 12/2003 | Humphrey |
| 7,010,340 B2 | 3/2006 | Scarantino et al. | 2003/0229371 A1 | 12/2003 | Whitworth |
| 7,029,438 B2 | 4/2006 | Morin et al. | 2004/0002735 A1 | 1/2004 | Lizardi et al. |
| 7,041,052 B2 | 5/2006 | Saadat et al. | 2004/0098007 A1 | 5/2004 | Heiss |
| 7,052,489 B2 | 5/2006 | Griego et al. | 2004/0116948 A1 | 6/2004 | Sixto, Jr. et al. |
| 7,060,024 B2 | 6/2006 | Long et al. | 2004/0133089 A1 | 7/2004 | Kilcoyne et al. |
| 7,060,025 B2 | 6/2006 | Long et al. | 2004/0138525 A1 | 7/2004 | Saadat et al. |
| 7,063,697 B2 | 6/2006 | Slater | 2004/0138529 A1 | 7/2004 | Wiltshire et al. |
| 7,066,879 B2 | 6/2006 | Fowler et al. | 2004/0138587 A1 | 7/2004 | Lyons, IV |
| 7,066,936 B2 | 6/2006 | Ryan | 2004/0186350 A1 | 9/2004 | Brenneman et al. |
| 7,070,602 B2 | 7/2006 | Smith et al. | 2004/0193186 A1 | 9/2004 | Kortenbach et al. |
| 7,076,305 B2 | 7/2006 | Imran et al. | 2004/0193188 A1 | 9/2004 | Francese |
| 7,083,629 B2 | 8/2006 | Weller et al. | 2004/0193189 A1 | 9/2004 | Kortenbach et al. |
| 7,087,071 B2 | 8/2006 | Nicholas et al. | 2004/0193200 A1 | 9/2004 | Dworschak et al. |
| 7,090,673 B2 | 8/2006 | Dycus et al. | 2004/0199052 A1 | 10/2004 | Banik et al. |
| 7,090,685 B2 | 8/2006 | Kortenbach et al. | 2004/0210245 A1 | 10/2004 | Erickson et al. |
| 7,101,371 B2 | 9/2006 | Dycus et al. | 2004/0215058 A1 | 10/2004 | Zirps et al. |
| 7,101,372 B2 | 9/2006 | Dycus et al. | 2004/0225186 A1 | 11/2004 | Horne, Jr. et al. |
| 7,101,373 B2 | 9/2006 | Dycus et al. | 2004/0230095 A1 | 11/2004 | Stefanchik et al. |
| 7,105,000 B2 | 9/2006 | McBrayer | 2004/0230096 A1 | 11/2004 | Stefanchik et al. |
| 7,105,005 B2 | 9/2006 | Blake | 2004/0230097 A1 | 11/2004 | Stefanchik et al. |
| 7,112,208 B2 | 9/2006 | Morris et al. | 2004/0249367 A1 | 12/2004 | Saadat et al. |
| 7,118,531 B2 | 10/2006 | Krill | 2004/0249394 A1 | 12/2004 | Morris et al. |
| 7,118,587 B2 | 10/2006 | Dycus et al. | 2005/0033277 A1 | 2/2005 | Clague et al. |
| 7,128,708 B2 | 10/2006 | Saadat et al. | 2005/0033333 A1 | 2/2005 | Smith et al. |
| RE39,415 E | 11/2006 | Bales et al. | 2005/0049026 A1 | 3/2005 | Rivera et al. |
| 7,131,978 B2 | 11/2006 | Sancoff et al. | 2005/0065397 A1 | 3/2005 | Saadat et al. |
| 7,137,980 B2 | 11/2006 | Buysse et al. | 2005/0065517 A1 | 3/2005 | Chin |
| 7,137,981 B2 | 11/2006 | Long | 2005/0070754 A1 | 3/2005 | Nobis et al. |
| 7,147,650 B2 | 12/2006 | Lee | 2005/0070763 A1 | 3/2005 | Nobis et al. |
| 7,153,321 B2 | 12/2006 | Andrews | 2005/0070764 A1 | 3/2005 | Nobis et al. |
| 7,163,525 B2 | 1/2007 | Franer | 2005/0080413 A1 | 4/2005 | Canady |
| 7,172,714 B2 | 2/2007 | Jacobson | 2005/0090837 A1 | 4/2005 | Sixto, Jr. et al. |
| 7,179,254 B2 | 2/2007 | Pendekanti et al. | 2005/0090838 A1 | 4/2005 | Sixto, Jr. et al. |
| 7,195,612 B2 | 3/2007 | Van Sloten et al. | 2005/0101837 A1 | 5/2005 | Kalloo et al. |
| 7,195,631 B2 | 3/2007 | Dumbauld | 2005/0101838 A1 | 5/2005 | Camillocci et al. |
| 7,208,005 B2 | 4/2007 | Frecker et al. | 2005/0107664 A1 | 5/2005 | Kalloo et al. |
| 7,223,272 B2 | 5/2007 | Francere et al. | 2005/0110881 A1 | 5/2005 | Glukhovsky et al. |
| 7,232,445 B2 | 6/2007 | Kortenbach et al. | 2005/0113847 A1 | 5/2005 | Gadberry et al. |
| 7,241,290 B2 | 7/2007 | Doyle et al. | 2005/0124855 A1 | 6/2005 | Jaffe et al. |
| 7,244,228 B2 | 7/2007 | Lubowski | 2005/0125010 A1 | 6/2005 | Smith et al. |
| 7,252,660 B2 | 8/2007 | Kunz | 2005/0131279 A1 | 6/2005 | Boulais et al. |
| 7,270,663 B2 | 9/2007 | Nakao | 2005/0131457 A1 | 6/2005 | Douglas et al. |
| 7,306,597 B2 | 12/2007 | Manzo | 2005/0137454 A1 | 6/2005 | Saadat et al. |
| 7,329,257 B2 | 2/2008 | Kanehira et al. | 2005/0143690 A1 | 6/2005 | High |
| 7,329,383 B2 | 2/2008 | Stinson | 2005/0149087 A1 | 7/2005 | Ahlberg et al. |
| 7,344,536 B1 | 3/2008 | Lunsford et al. | 2005/0149096 A1 | 7/2005 | Hilal et al. |
| 7,364,582 B2 | 4/2008 | Lee | 2005/0159648 A1 | 7/2005 | Freed |

| | | | | | | |
|---|---|---|---|---|---|---|
| 2005/0165378 A1 | 7/2005 | Heinrich et al. | | 2006/0259010 A1 | 11/2006 | Stefanchik et al. |
| 2005/0165411 A1 | 7/2005 | Orban, III | | 2006/0264752 A1* | 11/2006 | Rubinsky et al. ............ 600/439 |
| 2005/0165429 A1 | 7/2005 | Douglas et al. | | 2006/0264930 A1 | 11/2006 | Nishimura |
| 2005/0192598 A1 | 9/2005 | Johnson et al. | | 2006/0271102 A1 | 11/2006 | Bosshard et al. |
| 2005/0192602 A1 | 9/2005 | Manzo | | 2006/0276835 A1 | 12/2006 | Uchida |
| 2005/0209624 A1 | 9/2005 | Vijay | | 2006/0285732 A1 | 12/2006 | Horn et al. |
| 2005/0215858 A1 | 9/2005 | Vail, III | | 2006/0287644 A1 | 12/2006 | Inganas et al. |
| 2005/0234297 A1 | 10/2005 | Devierre et al. | | 2006/0287666 A1 | 12/2006 | Saadat et al. |
| 2005/0250990 A1 | 11/2005 | Le et al. | | 2007/0002135 A1 | 1/2007 | Glukhovsky |
| 2005/0251176 A1 | 11/2005 | Swanstrom et al. | | 2007/0015965 A1 | 1/2007 | Cox et al. |
| 2005/0261674 A1 | 11/2005 | Nobis et al. | | 2007/0016225 A1 | 1/2007 | Nakao |
| 2005/0267492 A1 | 12/2005 | Poncet et al. | | 2007/0032700 A1 | 2/2007 | Fowler et al. |
| 2005/0272975 A1 | 12/2005 | McWeeney et al. | | 2007/0032701 A1 | 2/2007 | Fowler et al. |
| 2005/0272977 A1 | 12/2005 | Saadat et al. | | 2007/0049800 A1 | 3/2007 | Boulais |
| 2005/0273084 A1 | 12/2005 | Hinman et al. | | 2007/0079924 A1 | 4/2007 | Saadat et al. |
| 2005/0277945 A1 | 12/2005 | Saadat et al. | | 2007/0106118 A1 | 5/2007 | Moriyama |
| 2005/0277951 A1 | 12/2005 | Smith et al. | | 2007/0112342 A1 | 5/2007 | Pearson et al. |
| 2005/0277952 A1 | 12/2005 | Arp et al. | | 2007/0112383 A1 | 5/2007 | Conlon et al. |
| 2005/0277954 A1 | 12/2005 | Smith et al. | | 2007/0112384 A1 | 5/2007 | Conlon et al. |
| 2005/0277955 A1 | 12/2005 | Palmer et al. | | 2007/0112385 A1 | 5/2007 | Conlon |
| 2005/0277956 A1 | 12/2005 | Francese et al. | | 2007/0118115 A1 | 5/2007 | Artale et al. |
| 2005/0277957 A1 | 12/2005 | Kuhns et al. | | 2007/0123840 A1 | 5/2007 | Cox |
| 2005/0283118 A1 | 12/2005 | Uth et al. | | 2007/0129719 A1 | 6/2007 | Kendale et al. |
| 2005/0288555 A1 | 12/2005 | Binmoeller | | 2007/0135709 A1 | 6/2007 | Rioux et al. |
| 2006/0004406 A1 | 1/2006 | Wehrstein et al. | | 2007/0156127 A1 | 7/2007 | Rioux et al. |
| 2006/0004409 A1 | 1/2006 | Nobis et al. | | 2007/0173869 A1 | 7/2007 | Gannoe et al. |
| 2006/0004410 A1 | 1/2006 | Nobis et al. | | 2007/0173870 A2 | 7/2007 | Zacharias |
| 2006/0015009 A1 | 1/2006 | Jaffe et al. | | 2007/0179525 A1 | 8/2007 | Frecker et al. |
| 2006/0020167 A1 | 1/2006 | Sitzmann | | 2007/0203487 A1 | 8/2007 | Sugita |
| 2006/0020247 A1 | 1/2006 | Kagan et al. | | 2007/0213754 A1 | 9/2007 | Mikkaichi et al. |
| 2006/0025654 A1 | 2/2006 | Suzuki et al. | | 2007/0225554 A1 | 9/2007 | Maseda et al. |
| 2006/0025819 A1 | 2/2006 | Nobis et al. | | 2007/0244358 A1 | 10/2007 | Lee |
| 2006/0041188 A1 | 2/2006 | Dirusso et al. | | 2007/0250057 A1 | 10/2007 | Nobis et al. |
| 2006/0058582 A1 | 3/2006 | Maahs et al. | | 2007/0255096 A1 | 11/2007 | Stefanchik et al. |
| 2006/0058776 A1 | 3/2006 | Bilsbury | | 2007/0255100 A1 | 11/2007 | Barlow et al. |
| 2006/0079890 A1 | 4/2006 | Guerra | | 2007/0255273 A1 | 11/2007 | Fernandez et al. |
| 2006/0089528 A1 | 4/2006 | Tartaglia et al. | | 2007/0255306 A1 | 11/2007 | Conlon et al. |
| 2006/0095060 A1 | 5/2006 | Mayenberger et al. | | 2007/0260112 A1 | 11/2007 | Rahmani |
| 2006/0111209 A1 | 5/2006 | Hinman et al. | | 2007/0260117 A1 | 11/2007 | Zwolinski et al. |
| 2006/0129166 A1 | 6/2006 | Lavelle | | 2007/0260273 A1 | 11/2007 | Cropper et al. |
| 2006/0135971 A1 | 6/2006 | Swanstrom et al. | | 2007/0270629 A1 | 11/2007 | Charles |
| 2006/0135984 A1 | 6/2006 | Kramer et al. | | 2007/0270889 A1 | 11/2007 | Conlon et al. |
| 2006/0142644 A1 | 6/2006 | Mulac et al. | | 2007/0270907 A1 | 11/2007 | Stokes et al. |
| 2006/0142790 A1 | 6/2006 | Gertner | | 2007/0282371 A1 | 12/2007 | Lee et al. |
| 2006/0149132 A1 | 7/2006 | Iddan | | 2008/0004650 A1 | 1/2008 | George |
| 2006/0149135 A1 | 7/2006 | Paz | | 2008/0015552 A1 | 1/2008 | Doyle et al. |
| 2006/0161190 A1 | 7/2006 | Gadberry et al. | | 2008/0027387 A1 | 1/2008 | Grabinsky |
| 2006/0167416 A1 | 7/2006 | Mathis et al. | | 2008/0086172 A1 | 4/2008 | Martin et al. |
| 2006/0167482 A1 | 7/2006 | Swain et al. | | 2008/0097483 A1 | 4/2008 | Ortiz et al. |
| 2006/0178560 A1 | 8/2006 | Saadat et al. | | 2008/0103527 A1 | 5/2008 | Martin et al. |
| 2006/0183975 A1 | 8/2006 | Saadat et al. | | 2008/0119870 A1 | 5/2008 | Williams |
| 2006/0189844 A1 | 8/2006 | Tien | | 2008/0125796 A1 | 5/2008 | Graham |
| 2006/0189845 A1 | 8/2006 | Maahs et al. | | 2008/0132892 A1 | 6/2008 | Lunsford et al. |
| 2006/0190027 A1 | 8/2006 | Downey | | 2008/0147113 A1 | 6/2008 | Nobis et al. |
| 2006/0195084 A1 | 8/2006 | Slater | | 2008/0171907 A1 | 7/2008 | Long et al. |
| 2006/0200005 A1 | 9/2006 | Bjork et al. | | 2008/0200755 A1 | 8/2008 | Bakos |
| 2006/0200169 A1 | 9/2006 | Sniffin | | 2008/0200762 A1 | 8/2008 | Stokes et al. |
| 2006/0200170 A1 | 9/2006 | Aranyi | | 2008/0200911 A1 | 8/2008 | Long |
| 2006/0200199 A1 | 9/2006 | Bonutti et al. | | 2008/0200933 A1 | 8/2008 | Bakos et al. |
| 2006/0217697 A1 | 9/2006 | Lau et al. | | 2008/0200934 A1 | 8/2008 | Fox |
| 2006/0217742 A1 | 9/2006 | Messerly et al. | | 2008/0221619 A1 | 9/2008 | Spivey et al. |
| 2006/0217743 A1 | 9/2006 | Messerly et al. | | 2008/0228213 A1 | 9/2008 | Blakeney et al. |
| 2006/0229639 A1 | 10/2006 | Whitfield | | 2008/0243106 A1 | 10/2008 | Coe et al. |
| 2006/0229640 A1 | 10/2006 | Whitfield | | 2008/0269782 A1 | 10/2008 | Stefanchik et al. |
| 2006/0237022 A1 | 10/2006 | Chen et al. | | 2008/0269783 A1 | 10/2008 | Griffith |
| 2006/0237023 A1 | 10/2006 | Cox et al. | | 2008/0275474 A1 | 11/2008 | Martin et al. |
| 2006/0253004 A1 | 11/2006 | Frisch et al. | | 2008/0275475 A1 | 11/2008 | Schwemberger et al. |
| 2006/0253039 A1 | 11/2006 | McKenna et al. | | 2008/0300547 A1 | 12/2008 | Bakos |
| 2006/0258907 A1 | 11/2006 | Stefanchik et al. | | 2008/0312506 A1 | 12/2008 | Spivey et al. |
| 2006/0258908 A1 | 11/2006 | Stefanchik et al. | | 2009/0054728 A1 | 2/2009 | Trusty |
| 2006/0258910 A1 | 11/2006 | Stefanchik et al. | | 2009/0062788 A1 | 3/2009 | Long et al. |
| 2006/0258954 A1 | 11/2006 | Timberlake et al. | | 2009/0062792 A1 | 3/2009 | Vakharia et al. |
| 2006/0258955 A1 | 11/2006 | Hoffman et al. | | 2009/0062795 A1 | 3/2009 | Vakharia et al. |

| | | | |
|---|---|---|---|
| 2009/0112059 | A1 | 4/2009 | Nobis |
| 2009/0112062 | A1 | 4/2009 | Bakos |
| 2009/0112063 | A1 | 4/2009 | Bakos et al. |
| 2009/0131751 | A1 | 5/2009 | Spivey et al. |
| 2009/0131932 | A1 | 5/2009 | Vakharia et al. |
| 2009/0131933 | A1 | 5/2009 | Ghabrial et al. |
| 2009/0143794 | A1 | 6/2009 | Conlon et al. |
| 2009/0149710 | A1 | 6/2009 | Stefanchik et al. |
| 2009/0177219 | A1 | 7/2009 | Conlon |
| 2009/0182332 | A1 | 7/2009 | Long et al. |
| 2009/0192344 | A1 | 7/2009 | Bakos et al. |

FOREIGN PATENT DOCUMENTS

| | | | |
|---|---|---|---|
| EP | 0086338 | A1 | 8/1983 |
| EP | 0724863 | B1 | 7/1999 |
| EP | 0760629 | B1 | 11/1999 |
| EP | 0818974 | B1 | 7/2001 |
| EP | 0836832 | B1 | 12/2003 |
| EP | 1402837 | A1 | 3/2004 |
| EP | 0744918 | B1 | 4/2004 |
| EP | 0931515 | B1 | 8/2004 |
| EP | 1411843 | B1 | 10/2004 |
| EP | 1150614 | B1 | 11/2004 |
| EP | 1477104 | A1 | 11/2004 |
| EP | 1481642 | A1 | 12/2004 |
| EP | 1493391 | A1 | 1/2005 |
| EP | 0848598 | B1 | 2/2005 |
| EP | 1281360 | B1 | 3/2005 |
| EP | 1568330 | A1 | 8/2005 |
| EP | 1452143 | B1 | 9/2005 |
| EP | 1616527 | A2 | 1/2006 |
| EP | 1006888 | B1 | 3/2006 |
| EP | 1013229 | B1 | 6/2006 |
| EP | 1721561 | A1 | 11/2006 |
| EP | 1153578 | B1 | 3/2007 |
| EP | 1334696 | B1 | 3/2007 |
| EP | 1769766 | A1 | 4/2007 |
| EP | 1518499 | B1 | 8/2008 |
| EP | 1994904 | A1 | 11/2008 |
| FR | 2731610 | A1 | 9/1996 |
| GB | 2403909 | A | 1/2005 |
| JP | 2003-235852 | A | 8/2003 |
| JP | 2005-121947 | A | 5/2005 |
| JP | 2005-261514 | A | 9/2005 |
| SU | 194230 | | 5/1967 |
| SU | 980703 | | 12/1982 |
| WO | WO 93/20760 | A1 | 10/1993 |
| WO | WO 93/20765 | A1 | 10/1993 |
| WO | WO 96/27331 | A1 | 9/1996 |
| WO | WO 96/39946 | A1 | 12/1996 |
| WO | WO 97/12557 | A1 | 4/1997 |
| WO | WO 99/09919 | A1 | 3/1999 |
| WO | WO 99/17661 | A1 | 4/1999 |
| WO | WO 99/30622 | A2 | 6/1999 |
| WO | WO 02/11621 | A1 | 2/2002 |
| WO | WO 03/045260 | A1 | 6/2003 |
| WO | WO 03/078721 | A2 | 9/2003 |
| WO | WO 2004/086984 | A1 | 10/2004 |
| WO | WO 2005/009211 | A2 | 2/2005 |
| WO | WO 2005/065284 | A2 | 7/2005 |
| WO | WO 2005/112810 | A2 | 12/2005 |
| WO | WO 2005/120363 | A1 | 12/2005 |
| WO | WO 2006/007399 | A1 | 1/2006 |
| WO | WO 2006/041881 | A2 | 4/2006 |
| WO | WO 2007/063550 | A2 | 6/2007 |
| WO | WO 2007/109171 | A2 | 9/2007 |
| WO | WO 2009/027065 | A1 | 3/2009 |

OTHER PUBLICATIONS

Michael S. Kavic, M. D., Natural Orifice Translumenal Endoscopic Surgery: "NOTES", JSLS, vol. 10, pp. 133-134 (2006).

Guido M. Sclabas, M.D., et al., "Endoluminal Methods for Gastrotomy Closure in Natural Orifice TransEnteric Surgery (NOTES)," Surgical Innovation, vol. 13(1), pp. 23-30, Mar. 2006.

Fritscher-Ravens, et al., "Transgastric Gastropexy and Haital Hernia Repair for GERD Under EUS Control: a Porcine Model," American Society for Gastrointestinal Endoscopy, Mar. 14, 2003.

Ogando, "Prototype Tools That Go With The Flow," Design News, Jul. 17, 2006.

Kennedy, et al., "High-Burst-Strength, Feedback-Controlled Bipolar Vessel Sealing," Surgical Endoscopy, vol. 12, pp. 876-878 (1998).

Collins et al., "Local Gene Therapy of Solid Tumors with GM-CSF and B7-1 Eradicates Both Treated and Distal Tumors," Cancer Gene Therapy, vol. 13, pp. 1061-1071 (2006).

J.D. Paulson, M.D., et al., "Development of Flexible Culdoscopy," The Journal of the American Association of Gynecologic Laparoscopists, Nov. 1999, vol. 6, No. 4, pp. 487-490.

H. Seifert, et al., "Retroperitoneal Endoscopic Debridement for Infected Peripancreatic Necrosis,"The Lancet, Research Letters, vol. 356, Aug. 19, 2000, pp. 653-655.

K.E. Mönkemüller, M.D., et al., "Transmural Drainage of Pancreatic Fluid Collections Without Electrocautery Using the Seldinger Technique," Gastrointestinal Endoscopy, vol. 48, No. 2, 1998, pp. 195-200, (Received Oct. 3, 1997; Accepted Mar. 31, 1998).

D. Wilhelm et al., "An Innovative, Safe and Sterile Sigmoid Access (ISSA) for NOTES," Endoscopy 2007, vol. 39, pp. 401-406.

U.S. Appl. No. 12/413,479, filed Mar. 27, 2009.

U.S. Appl. No. 12/468,462, filed May 19, 2009.

Partial International Search Report for PCT/US2008/053973, Oct. 16, 2008 (2 pages).

International Search Report for PCT/US2008/053973, Dec. 22, 2008 (9 pages).

K. Sumiyarna et al., "Transesophageal Mediastinoscopy by Submucosal Endoscopy With Mucosal Flap Safety Value Technique," Gastrointest Endosc., Apr. 2007, vol. 65(4), pp. 679-683 (Abstract).

K. Sumiyama et al., "Submucosal Endoscopy with Mucosal Flap Safety Valve," Gastrointest Endosc. Apr. 2007, vol. 65(4) pp. 694-695 (Abstract).

K. Sumiyama et al., "Transgastric Cholecystectomy: Transgastric Accessibility to the Gallbladder Improved with the SEMF Method and a Novel Multibending Therapeutic Endoscope," Gastrointest Endosc., Jun. 2007, vol. 65(7), pp. 1028-1034 (Abstract).

K. Sumiyama et al., "Endoscopic Caps," Tech. Gastrointest. Endosc., vol. 8, pp. 28-32, 2006.

"Z-Offset Technique Used in the Introduction of Trocar During Laparoscopic Surgery," M.S. Hershey NOTES Presentation to EES NOTES Development Team, Sep. 27, 2007.

F.N. Denans, Nouveau Procede Pour La Guerison Des Plaies Des Intestines. Extrait Des Seances De La Societe Royale De Medecine De Marseille, Pendant Le Mois De Decembre 1825, et le Premier Tremestre De 1826, Séance Du 24 Fevrier 1826. Recueil De La Societe Royale De Medecin De Marseille. Marseille: Impr. D'Achard, 1826; 1:127-31. (with English translation).

I. Fraser, "An Historical Perspective on Mechanical Aids in Intestinal Anastomosis," Surg. Gynecol. Obstet. (Oct. 1982), vol. 155, pp. 566-574.

M.E. Ryan et al., "Endoscopic Intervention for Biliary Leaks After Laparoscopic Cholecystectomy: A Multicenter Review," Gastrointest. Endosc., vol. 47(3), 1998, pp. 261-266.

C. Cope, "Creation of Compression Gastroenterostomy by Means of the Oral, Percutaneous, or Surgical Introduction of Magnets: Feasibility Study in Swine," J. Vasc Interv Radiol, (1995), vol. 6(4), pp. 539-545.

J.W. Hazey et al., "Natural Orifice Transgastric Endoscopic Peritoneoscopy in Humans: Initial Clinical Trial," Surg Endosc, (Jan. 2008), vol. 22(1), pp. 16-20.

N. Chopita et al., "Endoscopic Gastroenteric Anastamosis Using Magnets," Endoscopy, (2005), vol. 37(4), pp. 313-317.

C. Cope et al., "Long Term Patency of Experimental Magnetic Compression Gastroenteric Anastomoses Achieved with Covered Stents," Gastrointest Endosc, (2001), vol. 53, pp. 780-784.

H. Okajima et al., "Magnet Compression Anastamosis for Bile Duct Stenosis After Duct to Duct Biliary Reconstruction in Living Donor Liver Transplantation," Liver Transplantation (2005), pp. 473-475.

A. Fritscher-Ravens et al., "Transluminal Endosurgery: Single Lumen Access Anastamotic Device for Flexible Endoscopy," Gastrointestinal Endosc, (2003), vol. 58(4), pp. 585-591.

G.A. Hallenbeck, M.D. et al., "An Instrument for Colorectal Anastomosis Without Sutrues," Dis Col Rectum, (1963), vol. 5, pp. 98-101.

T. Hardy, Jr., M.D. et al., "A Biofragmentable Ring for Sutureless Bowel Anastomosis. An Experimental Study," Dis Col Rectum, (1985), vol. 28, pp. 484-490.

P. O'Neill, M.D. et al., "Nonsuture Intestinal Anastomosis," Am J. Surg, (1962), vol. 104, pp. 761-767.

C.P. Swain, M.D. et al., "Anastomosis at Flexible Endoscopy: An Experimental Study of Compression Button Gastrojejunostomy," Gastrointest Endosc, (1991), vol. 37, pp. 628-632.

J.B. Murphy, M.D., "Cholecysto-Intestinal, Gastro-Intestinal, Entero-Intestinal Anastomosis, and Approximation Without Sutures (original research)," Med Rec, (Dec. 10, 1892), vol. 42(24), pp. 665-676.

USGI® EndoSurgical Operating System—g-Prox® Tissue Grasper/Approximation Device; [online] URL: http://www.usgimedical.com/eos/components-gprox.htm—accessed May 30, 2008 (2 pages.).

Printout of web page—http://www.vacumed.com/zcom/product/Product.do?compid=27&prodid=852, #51 XX Low-Cost Permanent Tubes 2MM ID, Smooth Interior Walls, VacuMed, Ventura, California, Accessed Jul. 24, 2007.

Endoscopic Retrograde Cholangiopancreatogram (ERCP); [online] URL: http://www.webmd.com/digestive-disorders/endoscopic-retrograde-cholangiopancreatogram-ercp.htm; last updated: Apr. 30, 2007; accessed: Feb. 21, 2008 (6 pages).

ERCP; Jackson Siegelbaum Gastroenterology; [online] URL: http://www.gicare.com/pated/epdgs20.htm; accessed Feb. 21, 2008 (3 pages).

D.G. Fong et al., "Transcolonic Ventral Wall Hernia Mesh Fixation in a Porcine Model," Endoscopy 2007; 39: 865-869.

B. Rubinsky, Ph.D., "Irreversible Electroporation in Medicine," Technology in Cancer Research and Treatment, vol. 6, No. 4, Aug. 2007, pp. 255-259.

D.B. Nelson, MD et al., "Endoscopic Hemostatic Devices," Gastrointestinal Endoscopy, vol. 54, No. 6, 2001, pp. 833-840.

CRE™ Pulmonary Balloon Dilator; [online] URL: http://www.bostonscientific.com/Device.bsci?page=HCP_Overview&navRelId=1000.1003&method=D..., accessed Jul. 18, 2008 (4 pages).

U.S. Appl. No. 11/894,358, filed Aug. 21, 2007.
U.S. Appl. No. 11/897,676, filed Aug. 31, 2007.
U.S. Appl. No. 11/968,810, filed Jan. 3, 2008.
U.S. Appl. No. 11/981,070, filed Oct. 31, 2007.
U.S. Appl. No. 11/981,078, filed Oct. 31, 2007.
U.S. Appl. No. 11/981,134, filed Oct. 31, 2007.
U.S. Appl. No. 11/986,084, filed Nov. 20, 2007.
U.S. Appl. No. 11/986,420, filed Nov. 21, 2007.
U.S. Appl. No. 11/986,489, filed Nov. 21, 2007.
U.S. Appl. No. 11/998,370, filed Nov. 29, 2007.
U.S. Appl. No. 12/014,417, filed Jan. 5, 2008.
U.S. Appl. No. 12/019,461, filed Jan. 24, 2008.
U.S. Appl. No. 12/045,318, filed Mar. 10, 2008.
U.S. Appl. No. 12/109,673, filed Apr. 25, 2008.
U.S. Appl. No. 12/109,699, filed Apr. 25, 2008.
U.S. Appl. No. 12/115,916, filed May 6, 2008.
U.S. Appl. No. 12/122,031, filed May 16, 2008.
U.S. Appl. No. 12/129,784, filed May 30, 2008.
U.S. Appl. No. 12/129,880, filed May 30, 2008.
U.S. Appl. No. 12/130,010, filed May 30, 2008.
U.S. Appl. No. 12/130,023, filed May 30, 2008.
U.S. Appl. No. 12/130,224, filed May 30, 2008.
U.S. Appl. No. 12/130,652, filed May 30, 2008.
U.S. Appl. No. 12/133,109, filed Jun. 4, 2008.
U.S. Appl. No. 12/133,953, filed Jun. 5, 2008.
U.S. Appl. No. 12/163,255, filed Jun. 27, 2008.
U.S. Appl. No. 12/169,868, filed Jul. 9, 2008.
U.S. Appl. No. 12/170,862, filed Jul. 10, 2008.
U.S. Appl. No. 12/172,752, filed Jul. 14, 2008.
U.S. Appl. No. 12/172,766, filed Jul. 14, 2008.
U.S. Appl. No. 12/172,782, filed Jul. 14, 2008.
U.S. Appl. No. 12/192,372, filed Aug. 15, 2008.
U.S. Appl. No. 12/203,330, filed Sep. 3, 2008.
U.S. Appl. No. 12/197,749, filed Aug. 25, 2008.
U.S. Appl. No. 12/197,653, filed Aug. 25, 2008.
U.S. Appl. No. 12/202,740, filed Sep. 2, 2008.
U.S. Appl. No. 12/203,458, filed Sep. 3, 2008.
U.S. Appl. No. 12/201,812, filed Aug. 29, 2008.
U.S. Appl. No. 12/207,306, filed Sep. 9. 2008.
U.S. Appl. No. 12/243,334, filed Oct. 1, 2008.
U.S. Appl. No. 12/234,425, filed Sep. 19, 2008.
U.S. Appl. No. 12/060,601, filed Apr. 1, 2008.
U.S. Appl. No. 11/952,475, filed Dec. 7, 2007.
U.S. Appl. No. 12/277,975, filed Nov. 25, 2008.
U.S. Appl. No. 12/277,957, filed Nov. 25, 2008.
U.S. Appl. No. 12/332,938, filed Dec. 11, 2008.
U.S. Appl. No. 12/337,340, filed Dec. 17, 2008.
U.S. Appl. No. 12/352,451, filed Jan. 12, 2009.
U.S. Appl. No. 12/359,824, filed Jan. 26, 2009.
U.S. Appl. No. 12/352,375, filed Jan. 12, 2009.
U.S. Appl. No. 12/359,053, filed Jan. 23, 2009.
U.S. Appl. No. 12/362,826, filed Jan. 30, 2009.
U.S. Appl. No. 12/363,137, filed Jan. 30, 2009.
U.S. Appl. No. 12/364,172, filed Feb. 2, 2009.
U.S. Appl. No. 12/364,256, filed Feb. 2, 2009.

Ethicon, Inc., "Wound Closure Manual: Chapter 3 (The Surgical Needle)," 15 pages, (1994).

* cited by examiner

ELECTROPORATION ABLATION APPARATUS, SYSTEM, AND METHOD

CROSS REFERENCE TO RELATED APPLICATION

The present application is related to concurrently-filed U.S. patent application Ser. No. 11/706,591, entitled ELECTRICAL ABLATION APPARATUS, SYSTEM, AND METHOD, which is incorporated herein by reference in its entirety.

BACKGROUND

Electrical therapy techniques have been employed in medicine to treat pain and other and other conditions. Electrical ablation techniques have been employed in medicine for the removal of diseased tissue or abnormal growths from the body. Nevertheless, there is a need for improved medical instruments to electrically ablate or destroy diseased tissue or abnormal growths from the body, such as cancer tissue. There may be a need for such electrical therapy techniques to be performed endoscopically.

Electrical therapy probes comprising electrodes may be required to electrically treat diseased tissue. The electrodes may be introduced into the patient endoscopically to the tissue treatment region by passing the electrodes through the working channel of an endoscope.

SUMMARY

In one general aspect, the various embodiments are directed to an ablation device. In one embodiment, the ablation device comprises an elongate flexible member having a proximal end and a distal end. A first working channel is formed within the flexible member. A first diagnostic probe having a proximal end and distal end is located within the first working channel and extends through the distal end of the flexible member. A first electrode is connected to the distal end of the first diagnostic probe, the first electrode is adapted to be endoscopically located in a tissue treatment region. The first electrode is adapted to couple to an electrical waveform generator to receive an irreversible electroporation electrical waveform sufficient to ablate tissue located proximate to the first electrode.

FIGURES

The novel features of the various embodiments of the invention are set forth with particularity in the appended claims. The various embodiments of the invention, however, both as to organization and methods of operation, together with further objects and advantages thereof, may best be understood by reference to the following description, taken in conjunction with the accompanying drawings as follows.

DESCRIPTION

Figure 1:
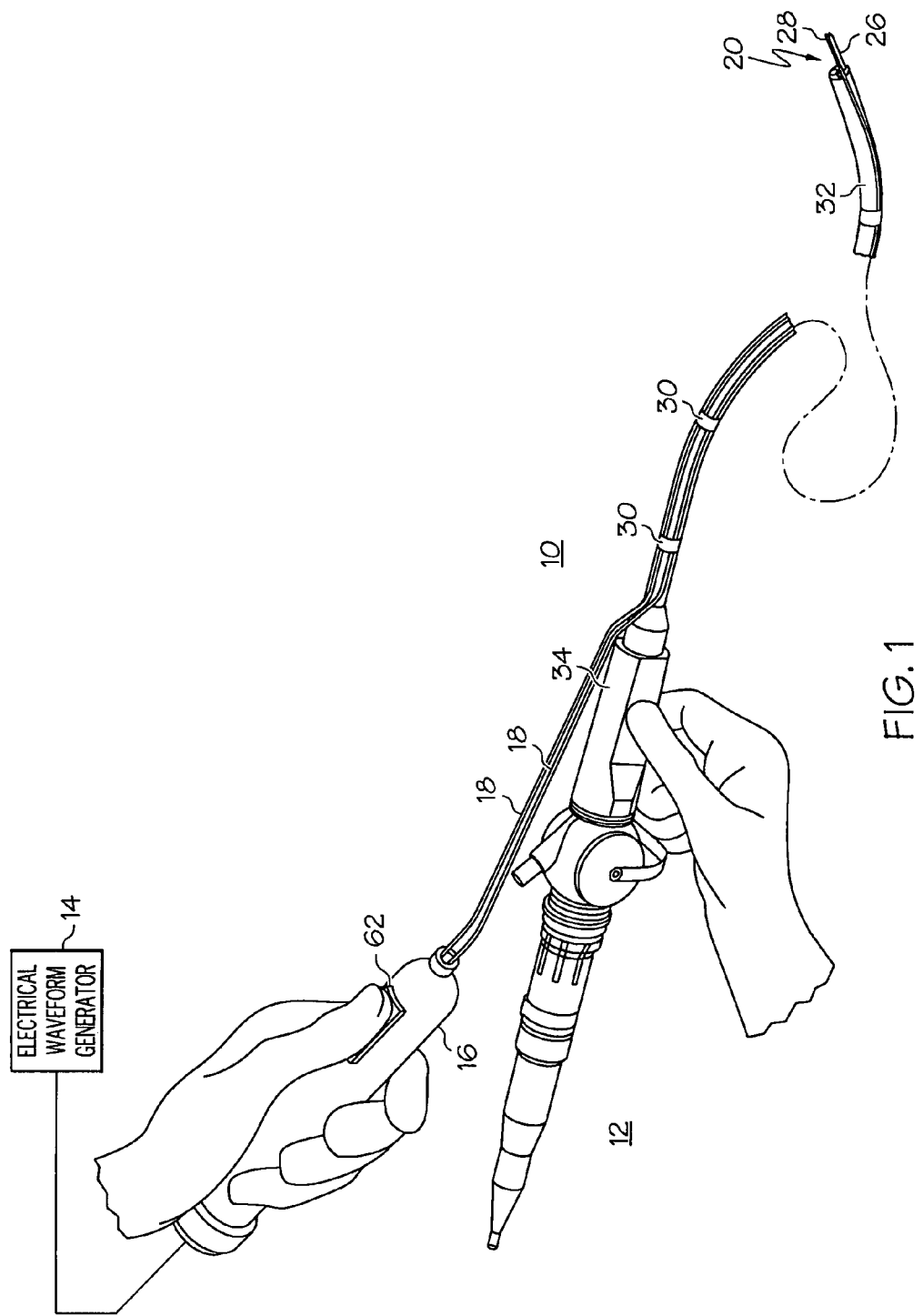
FIG. 1 illustrates one embodiment of an endoscopic ablation system.

The various embodiments described herein are directed to diagnostic and electrical therapy ablation devices. The diagnostic devices comprise biopsy probes. The electrical therapy ablation devices comprise probes and electrodes that can be positioned in a tissue treatment region of a patient endoscopically. An endoscopic electrode is inserted through a working channel of an endoscope. The placement and location of the electrodes can be important for effective and efficient therapy. Once positioned, the electrical therapy electrodes deliver electrical current to the treatment region. The electrical current is generated by a control unit or generator external to the patient and typically has particular waveform characteristics, such as frequency, amplitude, and pulse width. Depending on the diagnostic or therapeutic treatment rendered, the probes may comprise one electrode containing both a cathode and an anode or may contain a plurality of electrodes with at least one serving as a cathode and at least one serving as an anode.

Electrical therapy ablation may employ electroporation, or electropermeabilization, techniques where an externally applied electrical field significantly increases the electrical conductivity and permeability of a cell plasma membrane. Electroporation is the generation of a destabilizing electric potential across biological membranes. In electroporation, pores are formed when the voltage across the cell plasma membrane exceeds its dielectric strength. Electroporation destabilizing electric potentials are generally in the range of several hundred volts across a distance of several millimeters. Below certain magnitude thresholds, the electric potentials may be applied across a biological membrane as a way of introducing some substance into a cell, such as loading it with a molecular probe, a drug that can change the function of the cell, a piece of coding DNA, or increase the uptake of drugs in cells. If the strength of the applied electrical field and/or duration of exposure to it are properly chosen, the pores formed by the electrical pulse reseal after a short period of time, during which extra-cellular compounds have a chance to enter into the cell. Thus, below a certain threshold, the process is reversible and the potential does not permanently damage the cell membrane. This process may be referred to as reversible electroporation (RE).

On the other hand, the excessive exposure of live cells to large electrical fields (or potentials) can cause apoptosis and/or necrosis—the processes that result in cell death. Accordingly, this may be referred to irreversible electroporation (IRE) because the cells die when exposed to excessive electrical potentials across the cell membranes. The various embodiments described herein are directed to electrical therapy ablation devices such as electroporation ablation devices. In one embodiment, the electroporation ablation device may be an IRE device to destroy cells by applying an electric potential to the cell membrane. The IRE potentials may be applied to cell membranes of diseased tissue in order to kill the diseased cells. The IRE may be applied in the form of direct current (DC) electrical waveforms having a characteristic frequency, amplitude, and pulse width.

Electroporation may be performed with devices called electroporators, appliances which create the electric current and send it through the cell. The electroporators may comprise two or more metallic (e.g., Ag, AgCl) electrodes connected to an energy source to generate an electric field having a suitable characteristic waveform output in terms of frequency, amplitude, and pulse width.

Endoscopy means looking inside and refers to looking inside the human body for medical reasons. Endoscopy may be performed using an instrument called an endoscope. Endoscopy is a minimally invasive diagnostic medical procedure used to evaluate the interior surfaces of an organ by inserting a small tube into the body, often, but not necessarily, through a natural body opening. Through the endoscope, the operator is able to see abnormal or diseased tissue such as lesions and other surface conditions. The endoscope may have a rigid or a flexible tube or member and in addition to providing an image for visual inspection and photography, the endoscope enables taking biopsies, retrieving foreign objects, and introducing medical instruments to a tissue treatment region. Endoscopy is the vehicle for minimally invasive surgery.

The embodiments of the electrical therapy ablation devices may be employed for treating diseased tissue, tissue masses, tissue tumors, and lesions (diseased tissue). More particularly, the electrical therapy ablation devices may be employed in minimally invasive therapeutic treatment of diseased tissue. The electrical therapy ablation devices may be employed to deliver energy to the diseased tissue to ablate or destroy tumors, masses, legions, and other abnormal tissue growths. In one embodiment, the electrical therapy ablation devices and techniques described herein may be employed in the treatment of cancer by quickly creating necrosis of live tissue and destroying cancerous tissue in-vivo. These minimally invasive therapeutic treatment of diseased tissue where medical instruments are introduced to a tissue treatment region within the body of a patient through a natural opening are known as Natural Orifice Translumenal Endoscopic Surgery (NOTES)™.

A biopsy is a medical procedure involving the removal of cells or tissues for examination. The tissue is often examined under a microscope and can also be analyzed chemically (for example, using polymerase chain reaction [PCR] techniques). When only a sample of tissue is removed, the procedure is called an incisional biopsy or core biopsy. When an entire lump or suspicious area is removed, the procedure is called an excisional biopsy. When a sample of tissue or fluid is removed with a needle, the procedure is called a needle aspiration biopsy. A procedure called "optical biopsy" may be employed where optical coherence tomography may be adapted to allow high-speed visualization of tissue in a living animal with a catheter-endoscope 1 millimeter in diameter. Optical biopsy may be used to obtain cross-sectional images of internal tissues.

Biopsy specimens may be taken from part of a lesion when the cause of a disease is uncertain or its extent or exact character is in doubt. Vasculitis, for instance, is usually diagnosed on biopsy. Additionally, pathologic examination of a biopsy can determine whether a lesion is benign or malignant, and can help differentiate between different types of cancer.

FIG. 1 illustrates one embodiment of an endoscopic ablation system 10. The endoscopic ablation system 10 may be employed to electrically treat diseased tissue such as tumors and lesions. The endoscopic ablation system 10 may be configured to be positioned within a natural opening of a patient such as the colon or the esophagus and can be passed through the opening to a tissue treatment region. The illustrated endoscopic ablation system 10 may be used to treat diseased tissue via the colon or the esophagus of the patient, for example. The tissue treatment region may be located in the esophagus, colon, liver, breast, brain, and lung, among others. The endoscopic ablation system 10 can be configured to treat a number of lesions and ostepathologies including but not limited to metastatic lesions, tumors, fractures, infected site, inflamed sites, and the like. Once positioned at the target tissue treatment region, the endoscopic ablation system 10 can be configured to treat and ablate diseased tissue in that region. In one embodiment, the endoscopic ablation system 10 may be employed as a diagnostic instrument to collect a tissue sample using a biopsy device introduced into the tissue treatment region via an endoscope (e.g., the endoscopic ablation system 10). In one embodiment, the endoscopic ablation system 10 may be adapted to treat diseased tissue, such as cancers, of the gastrointestinal (GI) tract or esophagus that may be accessed orally. In another embodiment, the endoscopic ablation system 10 may be adapted to treat diseased tissue, such as cancers, of the liver or other organs that may be accessible transanally through the colon and/or the abdomen.

Figure 2:
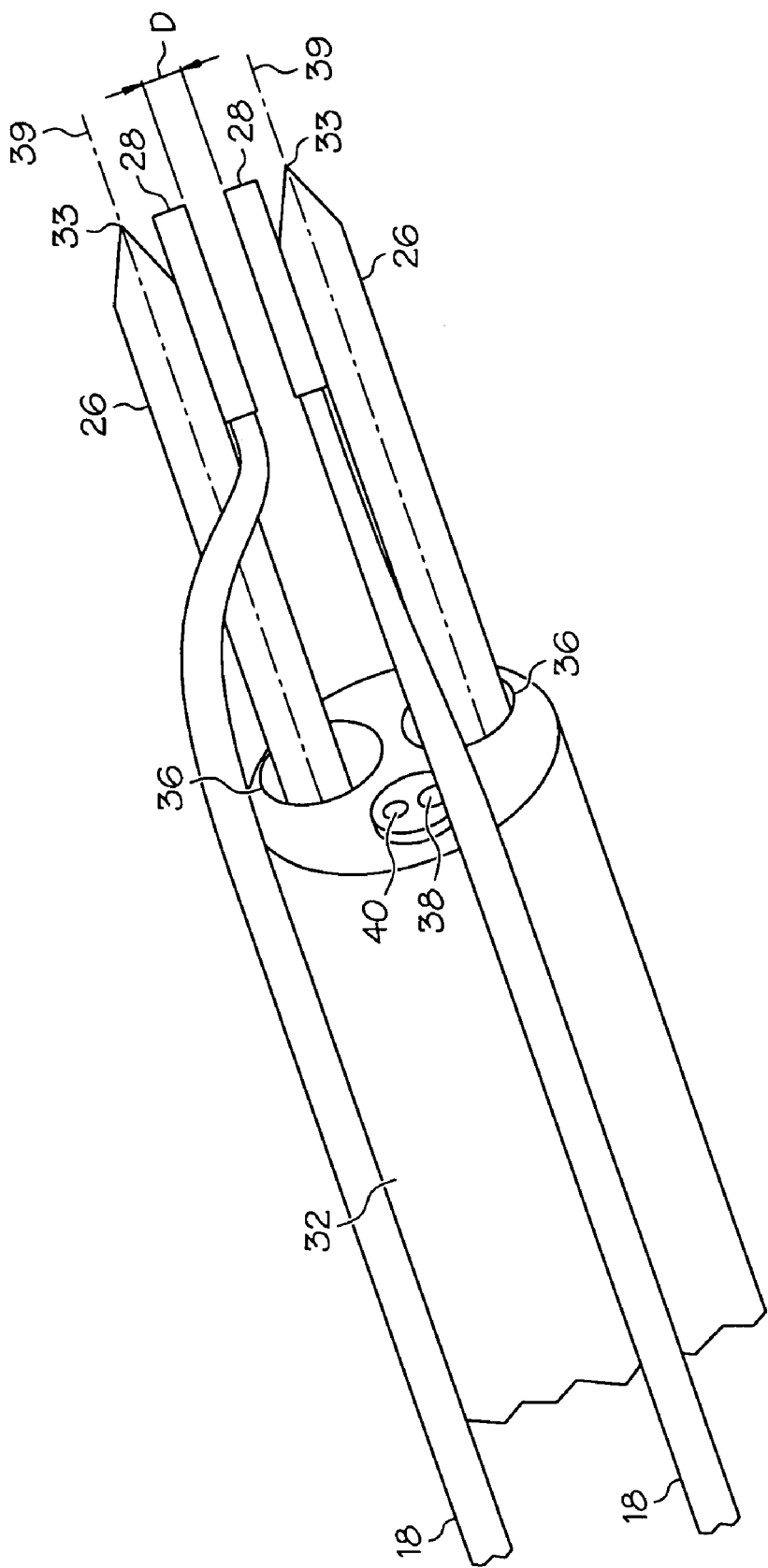
FIG. 2 is an enlarged view of one embodiment of a therapeutic/diagnostic probe of one embodiment of the endoscopic ablation system shown in FIG. 1.

One embodiment of the endoscopic ablation system 10 may be mounted on a flexible endoscope 12 (also referred to as endoscope 12), such as the GIF-100 model available from Olympus Corporation. The flexible endoscope 12 includes an endoscope handle 34 and a flexible shaft 32. The endoscopic ablation system 10 generally comprises one or more therapeutic/diagnostic probe 20, a plurality of conductors 18, a handpiece 16 having a switch 62, and an electrical waveform generator 14. In one embodiment, the electrical waveform generator 14 may be a high voltage direct current (DC) irreversible electroporation (IRE) generator. The therapeutic/diagnostic probe 20 is located at a distal end of the flexible shaft 32 and the conductors 18 attach to the flexible shaft 32 using a plurality of clips 30. The therapeutic/diagnostic probe 20 comprises an elongate member attached to an electrical energy delivery device comprising one or more electrical therapy electrodes 28. In one embodiment, the therapeutic/diagnostic probe 20 extends through a bore in the flexible shaft 32 such as a working channel 36 (FIG. 2). In one embodiment, the therapeutic/diagnostic probe 20 may comprise elongate diagnostic probes 26 attached or joined to the electrodes 28 that extend through the working channel 36. In another embodiment, the flexible shaft 32 may comprise two working channels 36 and a first diagnostic probe 26 joined to a first electrode 28 that extends through the distal end of a first working channels 36 and a second diagnostic probe 26 joined to a second electrode 28 that extends through the distal end of a second working channel 36. In one embodiment, the diagnostic probe comprises one or more diagnostic probes 26 attached or joined in any suitable manner to the electrodes 28. For example, the diagnostic probes 26 may be joined or attached to the electrodes 28 by welding, soldering, brazing or other well known techniques. Many different energy sources may be used for welding, soldering, or brazing such as, for example, a gas flame, an electric arc, a laser, an electron beam, friction, and ultrasound. Thus, in one embodiment, the therapeutic/diagnostic probe 20 may be employed in a diagnostic mode to take a biopsy sample of the diseased tissue using the diagnostic probes 26 and, in one embodiment the therapeutic/diagnostic probe 20 may be employed in a therapeutic mode by treating diseased tissue with electrical current delivered by the electrodes 28. In other embodiments, the therapeutic/diagnostic probe 20 may be employed in a combination of therapeutic and diagnostic modes. The therapeutic/diagnostic probe 20 may be passed though the one or more working channels 36 located within the flexible shaft 32. The therapeutic/diagnostic probe 20 is delivered to the tissue treatment region endoscopically and is located on top of the diseased tissue to be electrically treated. Once the therapeutic/diagnostic probe 20 is suitably located by the operator, manual operation of the switch 62 on the handpiece 16 electrically connects or disconnects the electrodes 28 to the electrical waveform generator 14. Alternatively, the switch 62 may be mounted on, for example, a foot switch (not shown).

In one embodiment, the electrical waveform generator 14 may be a conventional, bipolar/monopolar electrosurgical generator (ICC200 Erbe Inc.) or an IRE generator such as one of many models commercially available, including Model Number ECM800, available from BTX Boston, Mass. The IRE generator generates electrical waveforms having predetermined frequency, amplitude, and pulse width. The application of these electrical waveforms to the cell membrane causes the cell to die. The IRE electrical waveforms are applied to the cell membranes of diseased tissue in order to kill the diseased cells and ablate the diseased tissue. IRE electrical waveforms suitable to destroy the cells of diseased tissues energy are generally in the form of direct current (DC) electrical pulses delivered at a frequency in the range of 1-20 Hz, amplitude in the range of 100-1000 VDC, and pulse width in the range of 0.01-100 ms. For example, an electrical waveform having amplitude of 500 VDC and pulse duration of 20 ms may be delivered at a pulse repetition rate or frequency of 10 HZ can destroy a reasonably large volume of diseased tissue. Unlike RF ablation systems which require high power and energy input into the tissue to heat and destroy the tissue, IRE requires very little energy input into the tissue, rather the destruction of the tissue is caused by high electric fields. It has been determined that in order to destroy living tissue, the waveforms have to generate an electric field of at least 30,000V/m in the tissue treatment region. In one embodiment, the IRE generator 14 may generate voltages from about 100-1000 VDC. The IRE generator 14 may generate voltage pulses from 0.01-100 ms. These pulses may be generated at a suitable pulse repetition rate. The electrical current depends on the voltage amplitude, pulse width, pulse repetition rate, and the volume of tissue being treated. In one embodiment, the IRE generator 14 generates 20 ms pulses of 500 VDC amplitude between the electrodes 28. The embodiments, however, are not limited in this context.

When using the IRE generator 14 in monopolar mode with two or more electrical therapy electrodes 28, a grounding pad is not needed on the patient. Because a generator will typically be constructed to operate upon sensing connection of ground pad to the patient when in monopolar mode, it can be useful to provide an impedance circuit to simulate the connection of a ground pad to the patient. Accordingly, when the electrical ablation system 10 is used in monopolar mode without a grounding pad, an impedance circuit can be assembled by one skilled in the art, and electrically connected in series with one of the electrical therapy electrodes 28 that would otherwise be used with a grounding pad attached to a patient during monopolar electrosurgery. Use of an impedance circuit allows use of the IRE generator 14 in monopolar mode without use of a grounding pad attached to the patient.

FIG. 2 is an enlarged view of one embodiment of the therapeutic/diagnostic probe 20 of one embodiment of the endoscopic ablation system 10 shown in FIG. 1. The therapeutic/diagnostic probe 20 extends through the distal end of the flexible shaft 32. In one embodiment, the therapeutic/diagnostic probe 20 protrudes from the distal end of an internal lumen extending between the proximal and distal ends of the flexible endoscope 12. In one embodiment, the therapeutic/diagnostic probe 20 may comprise a biopsy device adapted and configured to remove sample tissue using an incisional, core, needle aspiration, or optical biopsy techniques. In one embodiment, the biopsy device comprises one or more diagnostic probes 26. As previously discussed, the electrical therapy electrodes 28 may be joined or attached to the diagnostic probes 26 in any suitable manner.

As previously discussed, the electrical therapy electrodes 28 are connected to the diagnostic probes 26 in any known suitable manner and are located in a spaced-apart relationship so as to define a distance D between the electrodes. The distance D is adjustable and can be increased or decreased by rotating one or both of the diagnostic probes 26. The therapeutic/diagnostic probe 20 are rotatable about a central axis 39. Thus, the diagnostic probes 26 and the electrodes 28 are rotatable about the central axis 39. The electrodes 28 may be rotated to increase or decrease the relative distance D between the electrode 28 either to focus the energy in a smaller tissue region or to enlarge the tissue treatment region. In this manner, the operator can surround the diseased tissue such as a cancerous lesion, a polyp, or a tumor. The electrodes 28 are energized with the electrical waveform generator 14 to treat the diseased tissue. The diagnostic probes 26 have a sharp tooth 33 at the distal end and are moveable from the distal end to the proximal end of the flexible shaft 32 capable of slicing a thin section of the tissue to obtain a biopsy sample (shown in more detail below). The diagnostic probes 26 may comprise a bore 35 (FIGS. 3A, B) at the distal end extending from a proximal end to the distal end of the diagnostic probes 26. Suction may be applied at the proximal end of the probes to remove a tissue sample before and/or after treatment through the bore 35 (FIGS. 3A, B) formed through the diagnostic probes 26.

The electrical therapy electrodes 28 may be positioned in any orientation relative to the diagnostic probes 26. The electrodes 28 and the diagnostic probes 26 may have any suitable shape. In the illustrated embodiment, the electrodes 28 may have a generally cuboidal shape and the diagnostic probes 26 may have an elongate cylindrical shape with a sharp tooth 33 and a bore 35 formed therein at the distal end. The electrical conductors 18 are electrically insulated from each other and surrounding structure except for the electrical connections the electrodes 28. The distal end of the flexible shaft 32 of the flexible endoscope 12 may comprise a light source 40, a viewing port 38, and one or more working channels 36. The viewing port 38 transmits an image within its field of view to an optical device such as a charge coupled device (CCD) camera within the flexible endoscope 12 so that an operator may view the image on a display monitor (not shown). In the embodiment shown in FIG. 2, the distal end of flexible shaft 32 is proximal to the electrodes 28 and is within the viewing field of the flexible endoscope 12 to enable the operator to see the diseased tissue to be treated between the electrodes 28.

Figure 3A:
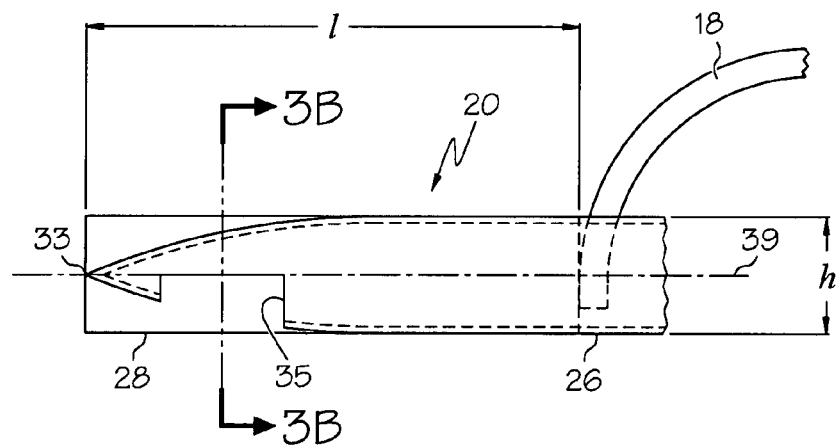
FIG. 3A is a side view of a distal end of one embodiment of a therapeutic/diagnostic probe comprising a biopsy probe and an electrical therapy electrode assembly.
Figure 3B:
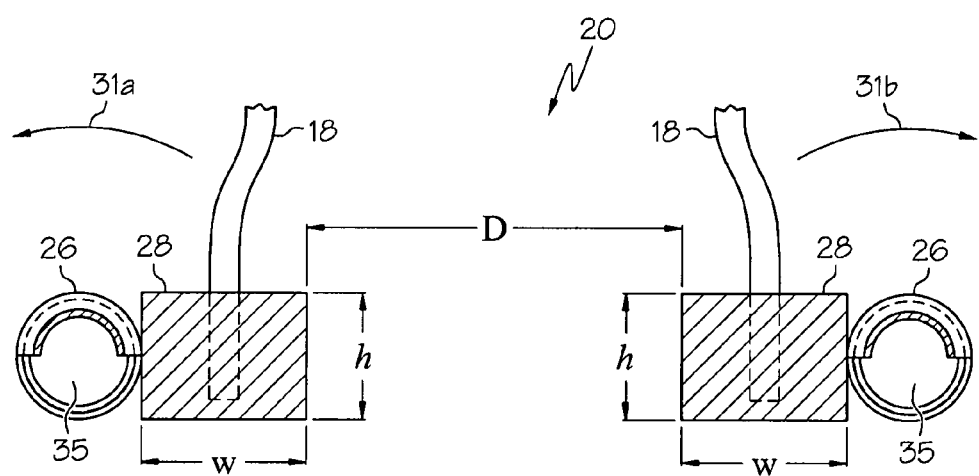
FIG. 3B is a sectional view of one embodiment of a therapeutic/diagnostic probe taken along section line 3B-3B showing the geometric relationship between the electrodes and the diagnostic probes.

FIG. 3A is a side view of the distal end of one embodiment of the therapeutic/diagnostic probe 20 comprising a biopsy probe 26 and an electrical therapy electrode 28 assembly. FIG. 3B is a sectional view of one embodiment of a therapeutic/diagnostic probe 20 taken along section line 3B-3B showing the geometric relationship between the electrodes 28 and the diagnostic probes 26. In the embodiment illustrated in FIGS. 3A, B, the cuboidal electrodes 28, each have a width "w," a length "l," and a thickness or height "h." The electrodes 28 have parallel, adjacent edges 8 separated by a distance "D." This geometry of the electrodes 28, the distance D between them, and the electrical waveform may be used to calculate an ablation index, which has particular significance to the location, size, shape, and depth of ablation achievable, as will be described later. The diagnostic probes 26 may be juxtaposed with the electrodes 28. In this embodiment, the two cylindrically elongate diagnostic probes 26 have a bore 35 for removing ablated tissue or taking biopsy samples of the tissue by way of suction. The length of the diagnostic probes 26 may extend through the entire length of the flexible endoscope 12. The conductors 18 are attached to the electrodes 28 in any suitable manner including welding, soldering, or brazing and may employ many different energy sources such as, for example, a gas flame, heat source, an electric arc, a laser, an electron beam, friction, and ultrasound. The electrodes 28 are attached to the diagnostic probes 26 and may be rotated about the central axis 39 in the directions indicated by arrows 31a and 31b.

Figure 4:
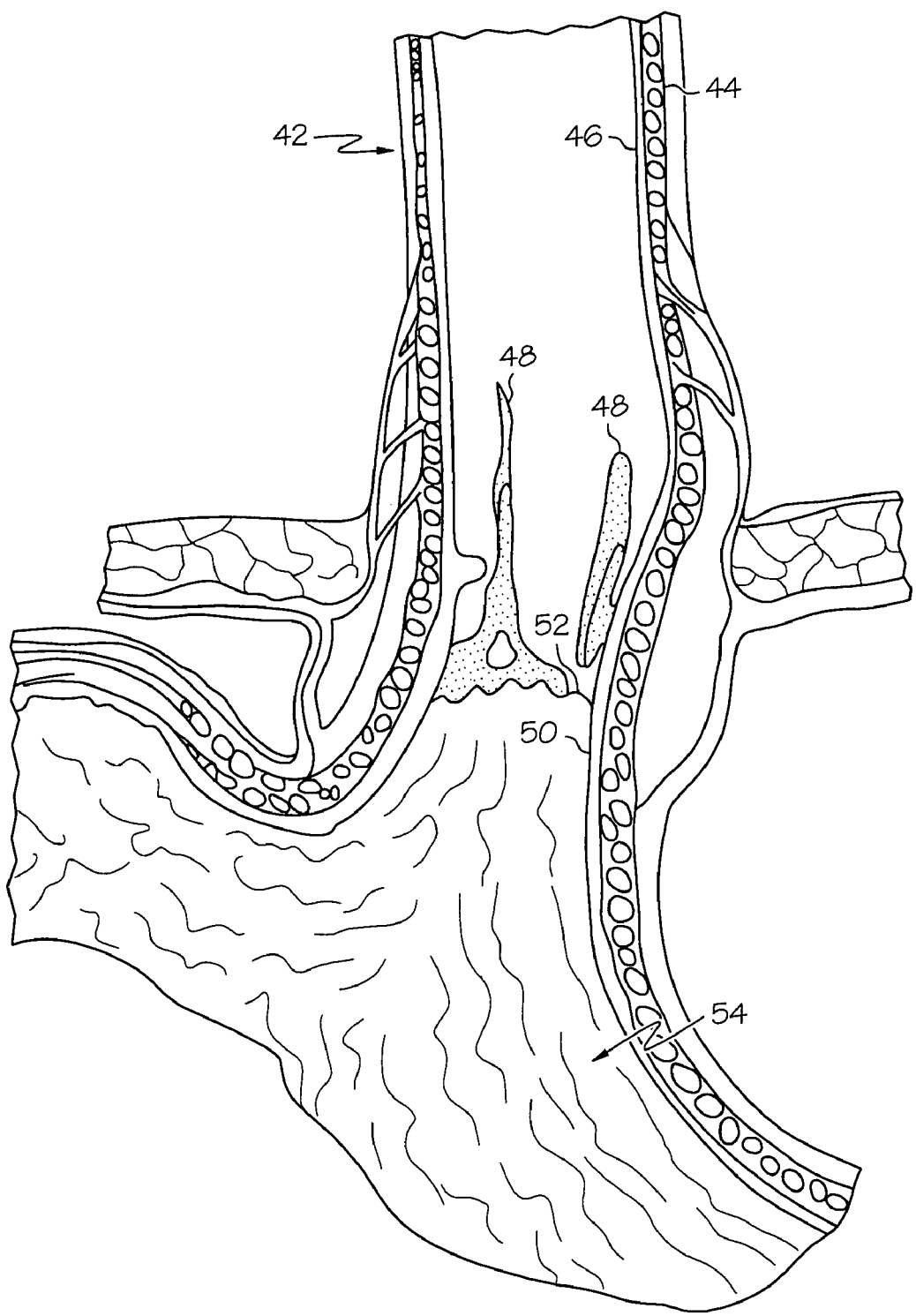
FIG. 4 is a sectional view of the lower end of an esophagus and the upper portion of a stomach of a human being.

FIG. 4 is a sectional view of the lower end of an esophagus 42 and the upper portion of a stomach 54 of a human being. The esophagus 42 has a mucosal layer 46, a muscular layer 44, and a region of diseased tissue 48. The boundary between the mucosal layer 46 of the esophagus 42 and a gastric mucosa 50 of the stomach 54 is a gastro-esophageal junction 52, which is approximately the location for the lower esophageal sphincter (LES). The LES allows food to enter the stomach 54 while preventing the contents of the stomach 54 from refluxing into the lower esophagus 42 and damaging the mucosal layer 46. The diseased tissue 48 can develop when chronic reflux is not treated. In one form, the diseased tissue 48 may be, for example, intestinal metaplasia, which is an early stage of Barrett's esophagus. As can be seen in FIG. 4, the esophagus 42 is relatively flaccid and contains numerous folds and irregularities on the interior lining.

Figure 5:
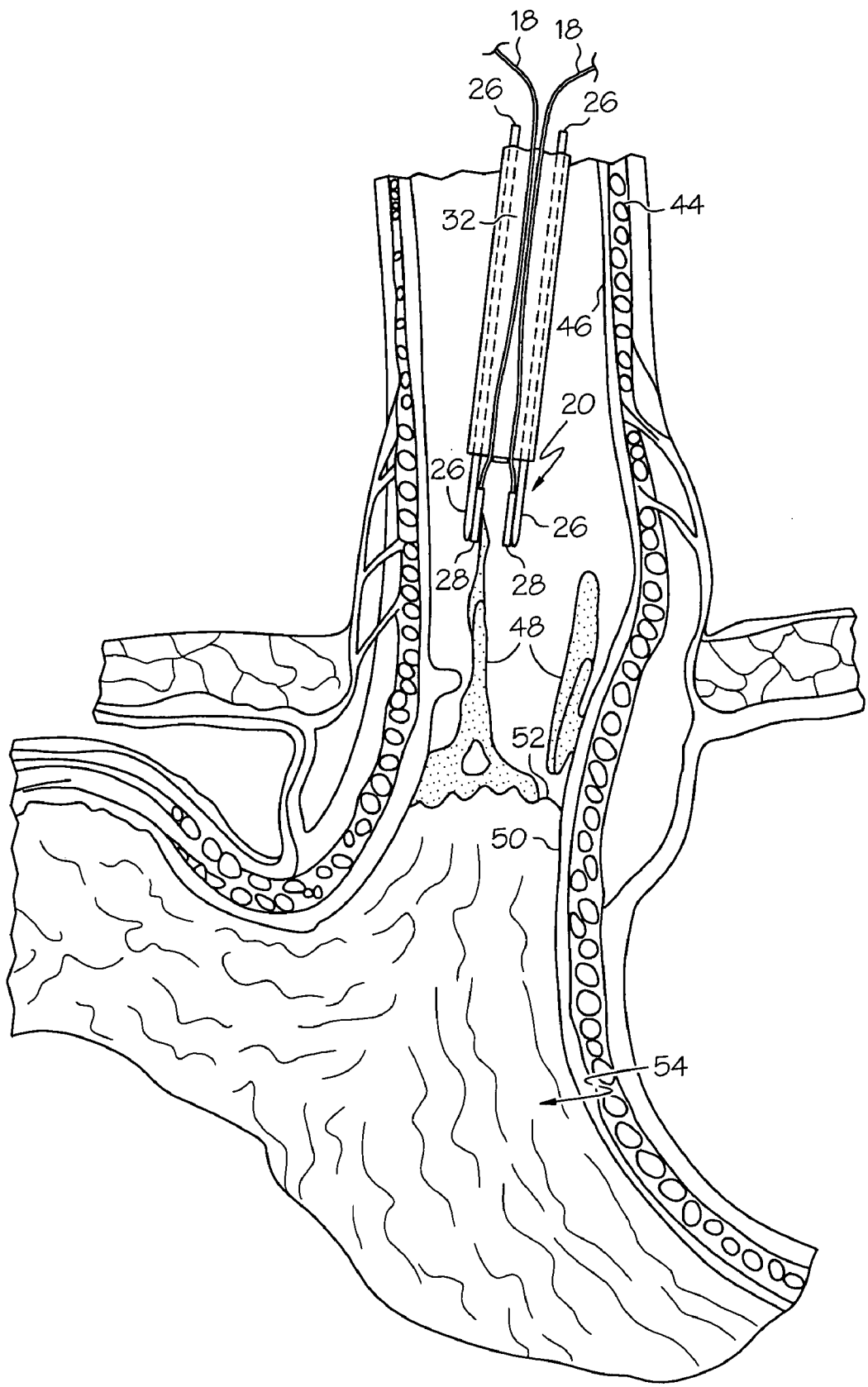
FIG. 5 illustrates the use of one embodiment of an endoscopic ablation system to treat diseased tissue in the lower esophagus.

FIG. 5 illustrates the use of one embodiment of the endoscopic ablation system 10 to treat the diseased tissue 48 in the lower esophagus 42. The operator positions the therapeutic/diagnostic probe 20 using endoscopic visualization so that the diseased tissue 48 to be treated is within the field of view of the flexible endoscope 12. Once the operator positions the therapeutic/diagnostic probe 20 such that the electrical therapy electrodes 28 are located above the diseased tissue 48, the operator may energize the electrodes 28 with the electrical waveform generator 14 to destroy the diseased tissue 48 in the tissue treatment region. For example, the electrodes 28 may be energized with an electrical waveform having amplitude of approximately 500 VDC and a pulse width of approximately 20 ms at a frequency of approximately 10 Hz. In this manner, the diseased tissue 48 in the tissue treatment region may be destroyed. This procedure may take very little time and may be repeated to destroy relatively larger portions of the diseased tissue 48. Suction may be applied to remove the treated tissue sample through the bore 35 formed in the diagnostic probes 26.

Figure 6:
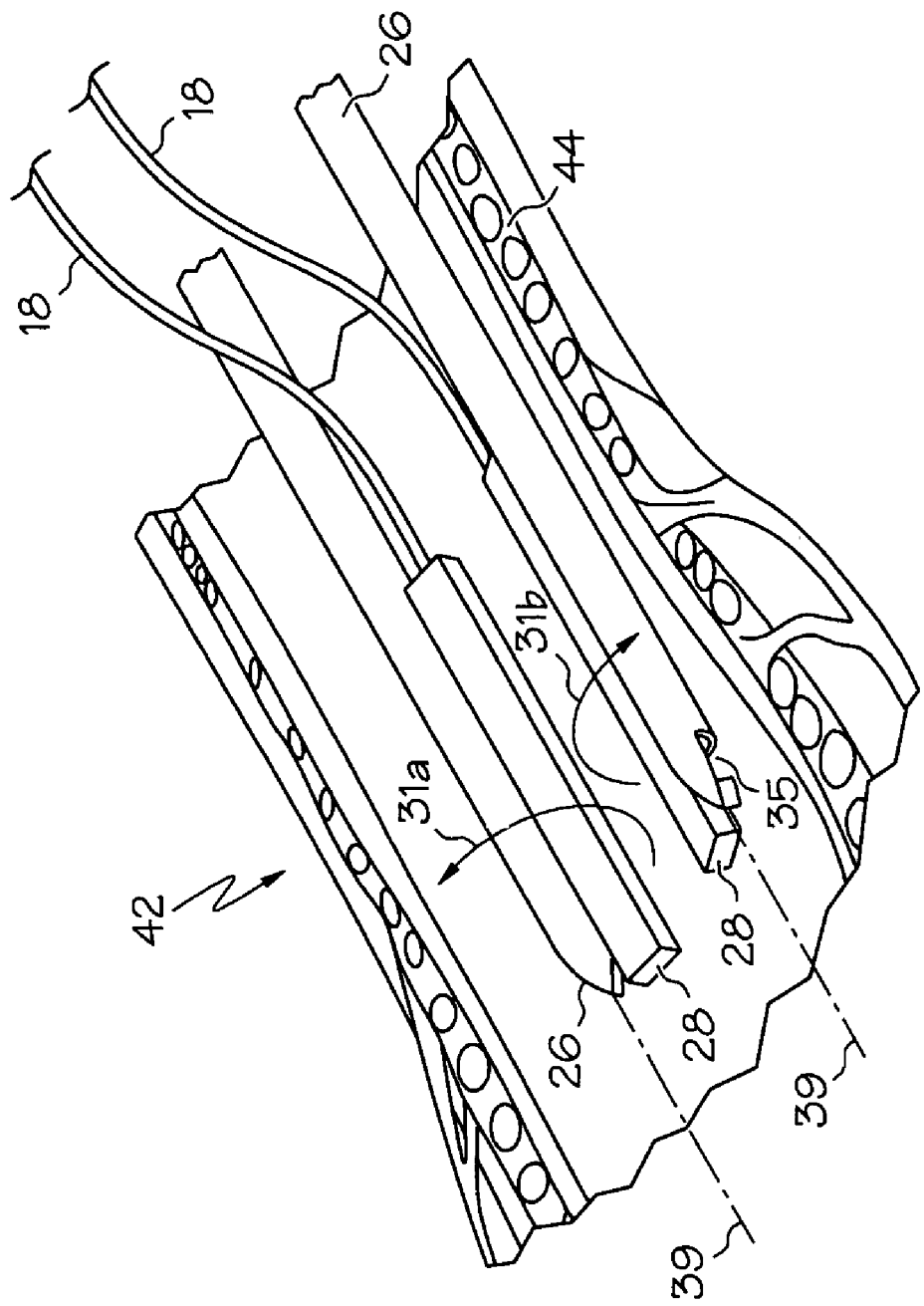
FIG. 6 illustrates the use of one embodiment of an endoscopic ablation system to treat diseased tissue in the lower esophagus.

FIG. 6 illustrates the use of the endoscopic ablation system 10 to treat the diseased tissue 48 in the lower esophagus 42. As shown in the illustrated embodiment, the electrical therapy electrodes 28 can be rotated about the central axis 39 in the direction indicated by arrows 31a and 31b. The treated tissue can be sucked into the bore 35 of the biopsy probe 26 by applying suction to thereto.

Figure 7:
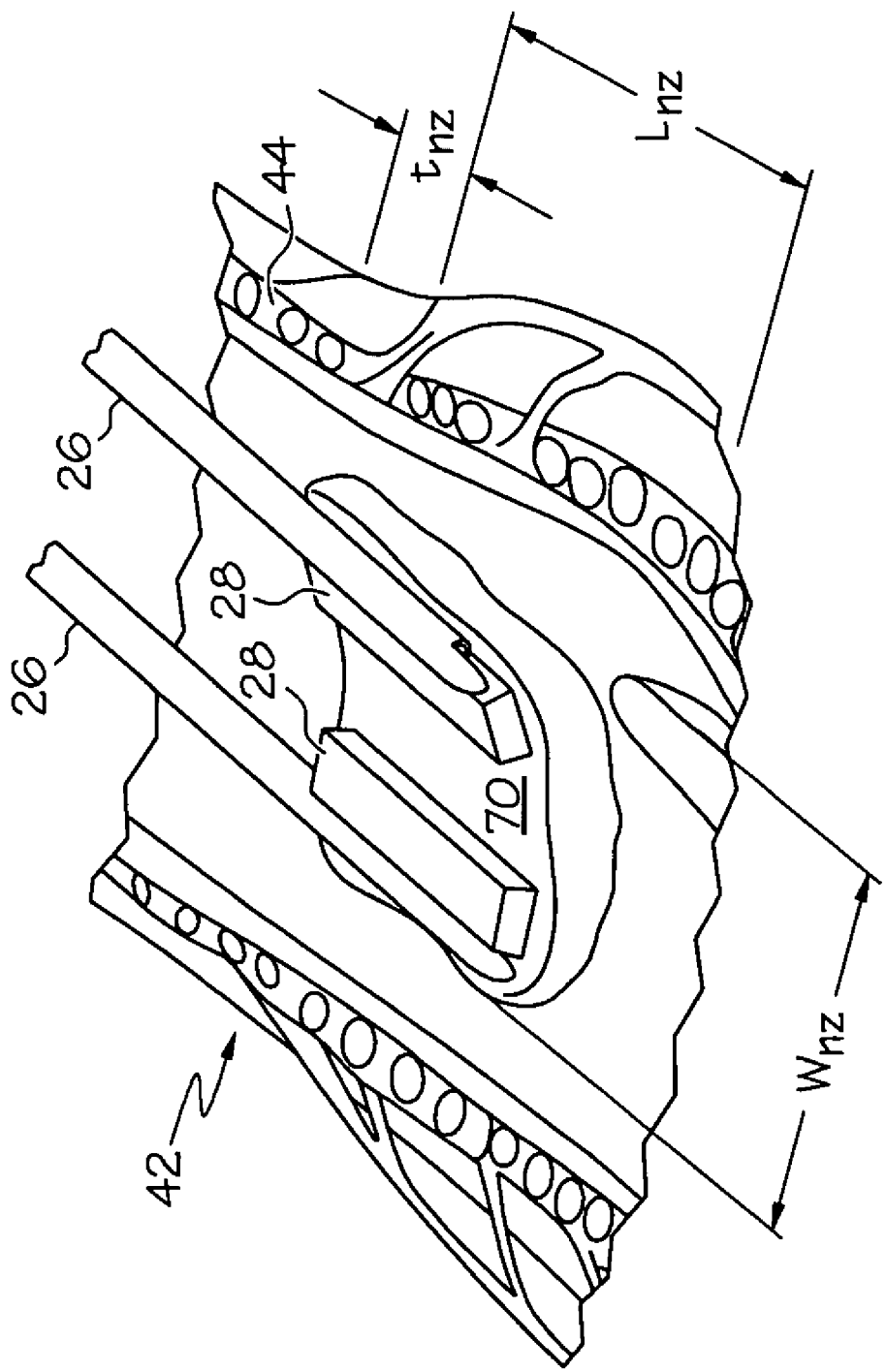
FIG. 7 illustrates one embodiment of a necrotic zone defined by the geometry and placement of the electrical therapy electrodes.

FIG. 7 illustrates one embodiment of a necrotic zone 70 defined by the geometry and placement of the electrical therapy electrodes 28. The energy delivered by the waveform to the electrodes 28 in terms of frequency, amplitude, and pulse width should be suitable to destroy the tissue in the necrotic zone 70. Based on the location and geometry of the electrodes 28, and the energy delivered thereto, the necrotic zone 70 in the illustrated embodiment may be approximated generally as a volume of width "wnz," a thickness "tnz," and a length "lnz." Energizing the electrodes 28 destroys the diseased tissue 48 within the necrotic zone 70. In one embodiment, electrodes 28 with a width "w=0.5 mm," a length "l=10 mm," and a thickness "h=0.5 mm" (as shown in FIGS. 3A, B) and a waveform of approximately 500 VDC, a pulse width of 20 ms, and a frequency of 10 Hz, would define a necrotic zone 70 with dimensions of approximately wnz=6 mm wide, lnz=10 mm long, and hnz=2 mm deep. If a biopsy indicates that the treatment region includes dysplastic or malignant cells, or if the treatment region is larger than the necrotic zone 70, the process may be repeated until all the diseased tissue 48 is destroyed in the treatment region and clean margins are recorded. In one embodiment, optical biopsy may be used as an alternative to the vacuum diagnostic probes 26 shown in the illustrated embodiments.

Figure 8:
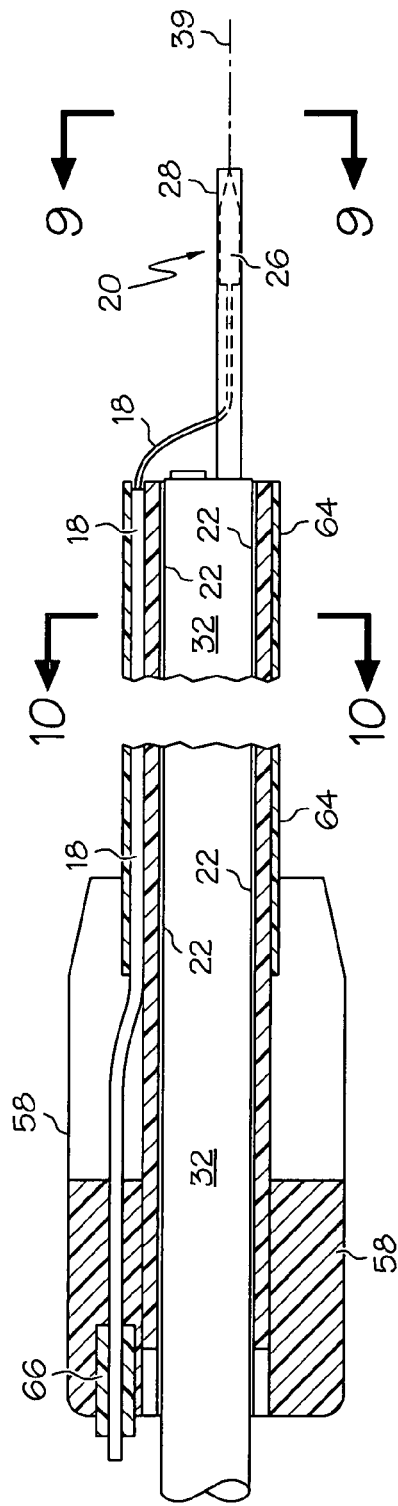
FIG. 8 is a sectional view taken along the longitudinal axis of one embodiment of an endoscopic ablation system shown in FIG. 1.

FIG. 8 is a sectional view taken along the longitudinal axis of one embodiment of an endoscopic ablation system 10 shown in FIG. 1. The distal portion of the flexible shaft 32 is located inside a rotation tube 22 of the endoscopic ablation system 10. The pair of electrical conductors 18 pass through a strain relief 66 of a rotation knob 58. In the illustrated embodiment an external tube 64 may be located over the flexible shaft 32 such that the conductors 18 pass between the external tube 64 and the rotation tube 22. Each of the conductors 18 connect electrically to the electrical therapy electrodes 28 in the therapeutic/diagnostic probe 20. The rotation tube 22 rotatably joins the rotation knob 58. The operator can rotatably orient the electrodes 28, even after insertion into the esophagus, by remotely rotating the diagnostic probes 26 about the central axis 39 of each of the therapeutic/diagnostic probe 20. The therapeutic/diagnostic probe 20 is within the field of view of the flexible endoscope 12, thus enabling the operator to see on a display monitor the tissue that is located between the electrodes 28. Optionally, in one embodiment, a valve element (not shown) may extend from the distal end of therapeutic/diagnostic probe 20 to prevent tissue or fluids from entering the therapeutic/diagnostic probe 20.

Figure 9:
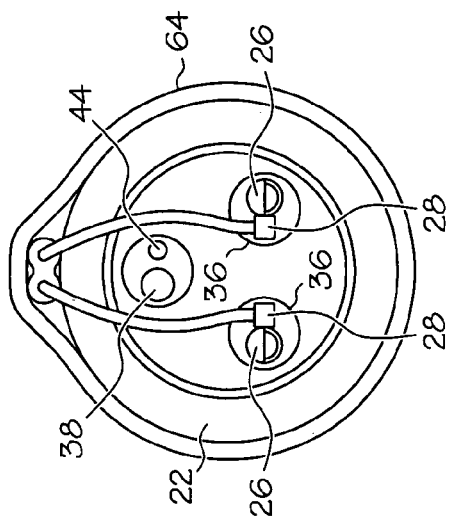
FIG. 9 is an end view taken along line 9-9 of one embodiment of a therapeutic/diagnostic probe of the endoscopic ablation system shown in FIG. 8.

FIG. 9 is an end view taken along line 9-9 of one embodiment of the therapeutic/diagnostic probe 20 of the endoscopic ablation system 10 shown in FIG. 8. The electrical conductors 18 connect to the electrical therapy electrodes 28. The rotation tube 22 retains the flexible shaft 32. The inside diameter of the rotation tube 22 is larger than the outer diameter of the flexible endoscope 12 to allow rotation of the rotation tube 22 while holding the flexible endoscope 12 stationary, or vice versa. Each of the therapeutic/diagnostic probe 20 comprising the diagnostic probes 26 attached to the electrodes 28 extend outwardly from the distal end of the flexible shaft 32 through each of the working channels 36. In this embodiment, the operator may endoscopically view the tissue between the electrodes 28. The flexible endoscope 12 includes the light source 40, the viewing port 38, and the one or more working channels 36.

Figure 10:
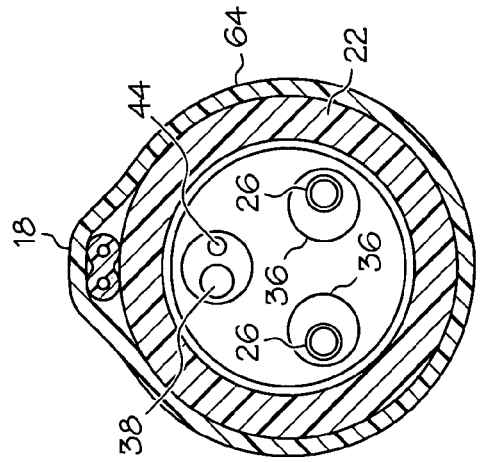
FIG. 10 is a sectional view taken along line 10-10 of a rotation tube of the endoscopic ablation system shown in FIG. 8.

FIG. 10 is a sectional view taken along line 10-10 of the rotation tube 22 of the endoscopic ablation system 10 shown in FIG. 8. The external tube 64 and the rotation tube 22 assemble and retain the electrical conductors 18 as already described. The light source 40, the viewing port 38, and the one or more working channels 36 of the flexible endoscope 12 are shown.

Figure 11:
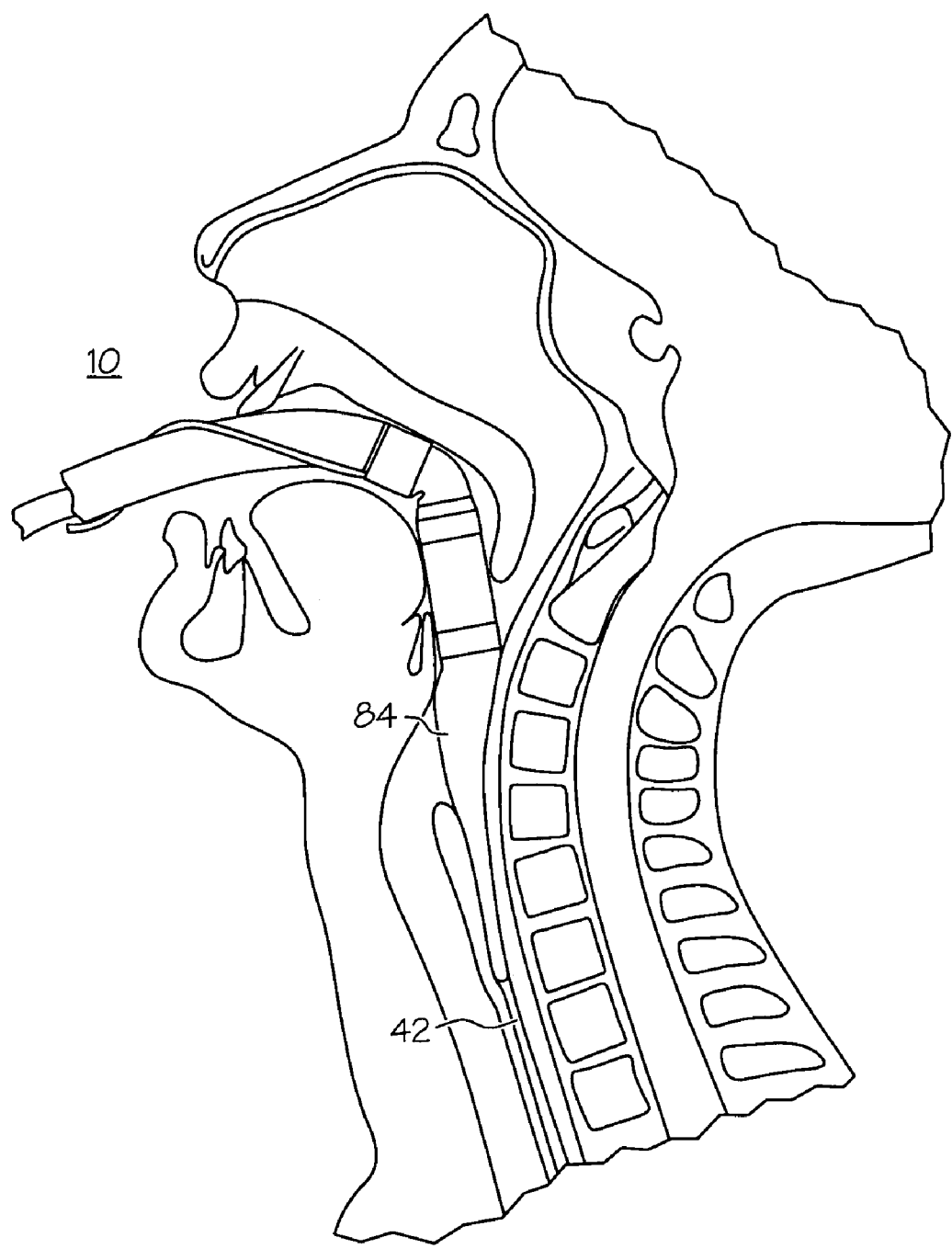
FIG. 11 shows one embodiment of a distal portion of an endoscopic ablation system shown in FIG. 1 partially inserted into the esophagus of a patient.

FIG. 11 shows one embodiment of the distal portion of the endoscopic ablation system 10 shown in FIG. 1 partially inserted into the esophagus 42 of a patient. A tapered end cover 84 dilates the esophagus 42 as the operator gently inserts the therapeutic/diagnostic probe 20 for positioning near the diseased tissue 48 to be ablated. A flexible coupling 88 flexes as shown, reducing the required insertion force and minimizing trauma (and post-procedural pain).

The operator may treat the diseased tissue 48 using the embodiment of the endoscopic ablation system 10 comprising the therapeutic/diagnostic probe 20 shown in FIGS. 1-3 and 5-11 as follows. The operator inserts the flexible shaft 32 of the endoscope 12 into the lower esophagus 42 trans-orally. A rigid support member at the distal end of the endoscope 12 holds the lower esophagus 42 open as the operator uses endoscopic visualization through the therapeutic/diagnostic probe 20 to position the electrical therapy electrodes 28 next to the diseased tissue 48 to be treated. The rigid support member opens and supports a portion of the flaccid, lower esophagus 42 and helps to bring the diseased tissue 48 to be treated into intimate contact with the electrodes 28 and within the field of view of the flexible endoscope 12. While watching through the viewing port 38, the operator actuates the switch 62, electrically connecting the electrodes 28 to the electrical waveform generator 14 through the electrical conductors 18. Electric current then passes through the portion of the diseased tissue 48 positioned between the electrodes 28 and within the field of view. When the operator observes that the tissue in the field of view has been ablated sufficiently, the operator deactuates the switch 62 to stop the ablation. The operator may reposition the electrodes 28 for subsequent tissue treatment, or may withdraw the therapeutic/diagnostic probe 20 (together with the flexible endoscope 12).

Figure 12:
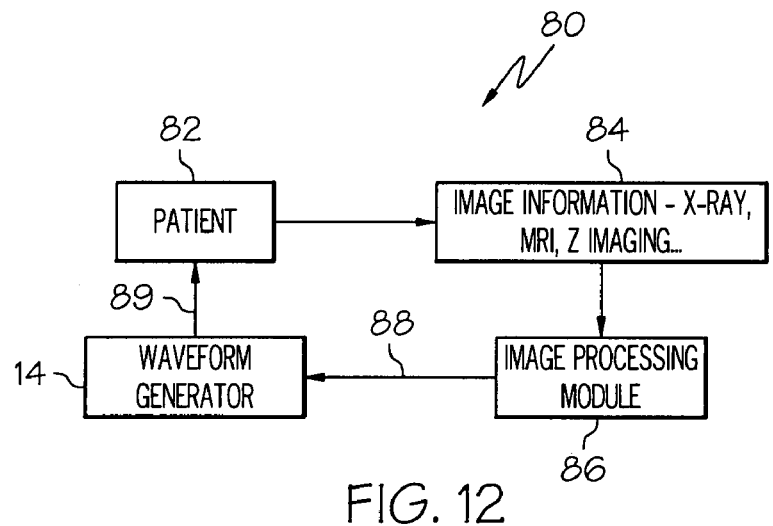
FIG. 12 is a diagram of one embodiment of a control loop for one embodiment of an irreversible electroporation therapy procedure to treat diseased tissue as described herein.

FIG. 12 is a diagram of one embodiment of a control loop 80 for one embodiment of an IRE therapy procedure to treat diseased tissue as described herein. As previously discussed, the IRE therapy may be effective in quickly creating necrosis of live tissue and destroying diseased (e.g., cancerous) tissue in-vivo. Real time information feedback about the size in volume of a necrotic zone may be helpful during an IRE therapy procedure for focal treatment of diseased tissue 48.

Prior to an IRE therapy procedure, a patient 82 will have an image of the diseased tissue 48 taken for clinical purposes in an effort to reveal, diagnose, or examine the diseased tissue 48 and to identify its location more precisely. The image information 84 will generally include geometric information about the volume of the diseased tissue 48. The image information 84 is provided to an image processing module 86 to calculate the volume of the diseased tissue 48 and to display a virtual model of the diseased tissue 48 on a monitor. The image processing module 86 may comprise, for example, image processing software applications such as Comsol Multiphysics available by Comsol, Inc. to receive the image information 84, extract the geometric information, and determine (e.g., calculate) the voltage required to treat the proper volume and outline of the necrotic zone required to treat the diseased tissue 48. The image processing module 86 creates a virtual model of a treatment zone necessary to treat the diseased tissue 48. The image processing module 86 then determines waveform parameters 88 of a suitable electrical waveform necessary to destroy the diseased tissue 48. The waveform parameters 88 include the frequency, amplitude, and pulse width of the electrical waveform to be generated by the waveform generator 14. The waveform generator 14 would then generate the suitable electrical waveform to destroy the diseased tissue 48 based on the calculated waveform parameters 88.

The image processing module 86 also comprises image processing software applications such as Matlab available by MathWorks, Inc. to receive the image information 84 and the virtual model and display an image of the diseased tissue 48 overlaid with an image of the virtual model. The overlaid images enable the operator to determine whether the calculated electrical waveform parameters 88 are suitable for destroying the diseased tissue 48, whether too strong or too weak. Thus, the IRE waveform parameters 88 may be adjusted such that the virtual model image substantially overlays the entire diseased tissue image. The calculated parameters 88 are provided to the waveform generator 14 and the diseased tissue may be treated with an electrical waveform 89 based on the calculated parameters 88 as discussed herein. After the diseased tissue 48 is treated with the electrical waveform 89, a new image of the diseased tissue 48 can be generated to determine the extent or effectiveness of the treatment. The cycle may be repeated as necessary to ablate the diseased tissue 48 as much as possible.

Figure 13:
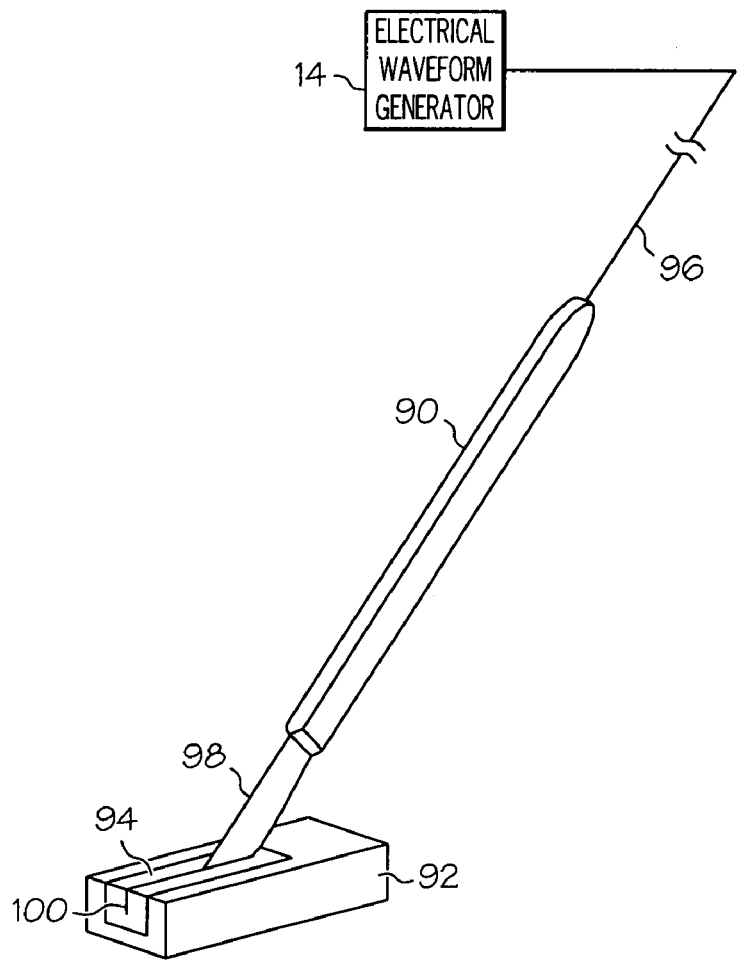
FIG. 13 illustrates one embodiment of an electrical scalpel for dissecting tissue.

FIG. 13 illustrates one embodiment of an electrical scalpel 90 for dissecting tissue 92. In one embodiment, the electrical scalpel 90 may be driven by an IRE waveform previously described. The scalpel 90 comprises a blade 98 that is formed of metal such as hardened and tempered steel (and/or stainless in many applications). The blade 98 is connected to the electrical waveform generator 14 by multiple electrical conductors 96. The electrical waveform generator 14 may generate an IRE waveform (e.g., 10 Hz frequency, 500 VDC amplitude, and 20 ms pulse). As the blade 98 dissects the tissue 92 along an incision 100, the electrical waveform generator 14 may be activated or pulsed to create a tissue destruction zone 94 surrounding the blade 98. Accordingly, as the blade 98 dissects the diseased tissue 92 it generates the tissue destruction zone 94 beyond the incision 100. This may help to ensure the destruction of any diseased tissue cells left behind. The pulse repetition rate or frequency of the electrical waveform generated by the generator 14 may be selected to provide a continuous zone of tissue destruction 94 as the blade 98 moves through the diseased tissue 92. In one embodiment, a feedback signal (e.g., audio, visual, or cut-off of electrical power to the blade 98) may be provided to the operator to indicate that the scalpel 90 is moving too quickly.

Figure 14:
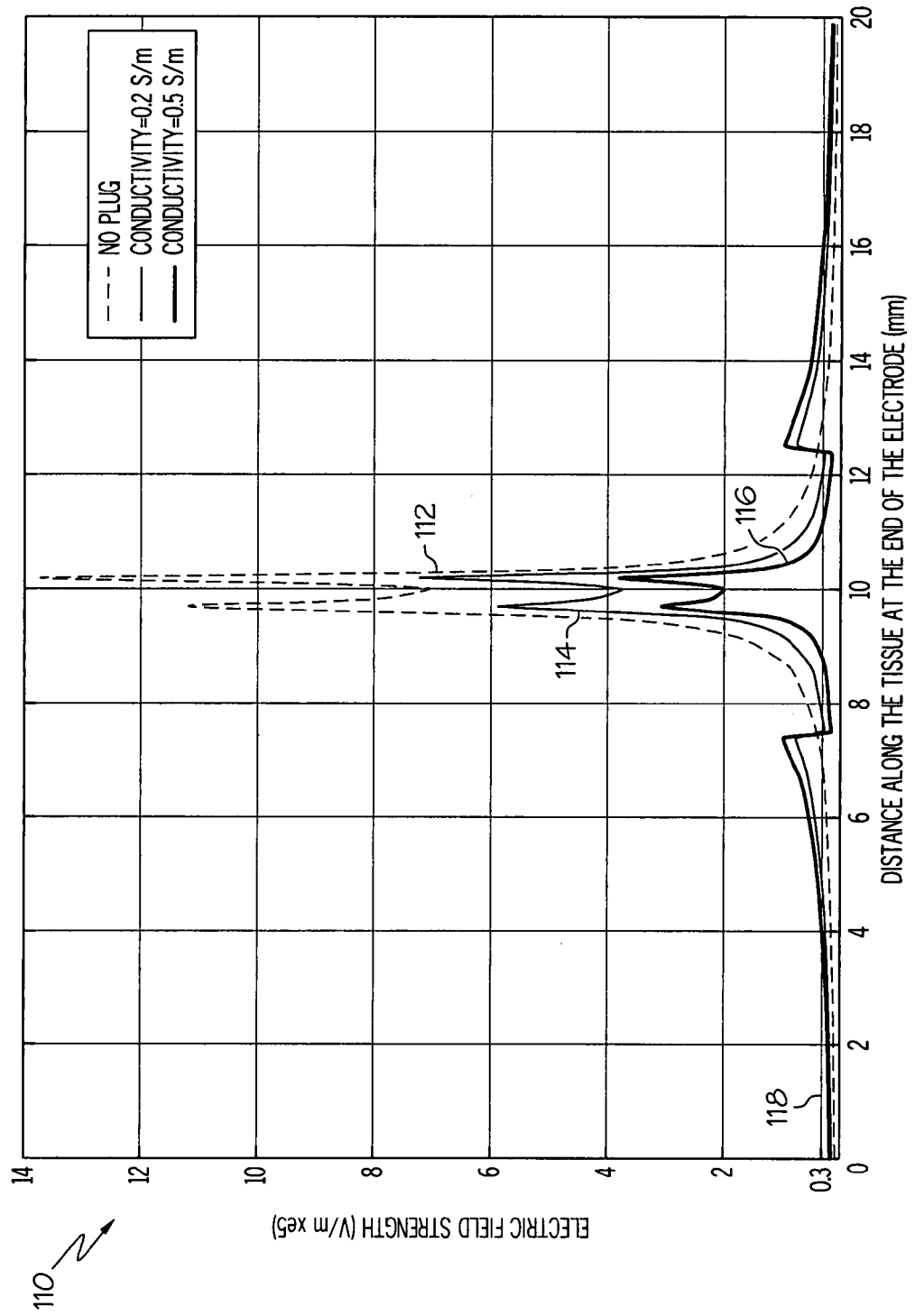
FIG. 14 is a graphical representation (graph) of electric field strength (along the y-axis) as a function of distance from an electrical therapy electrode under various conductivity environments near diseased tissue.
Figure 15:
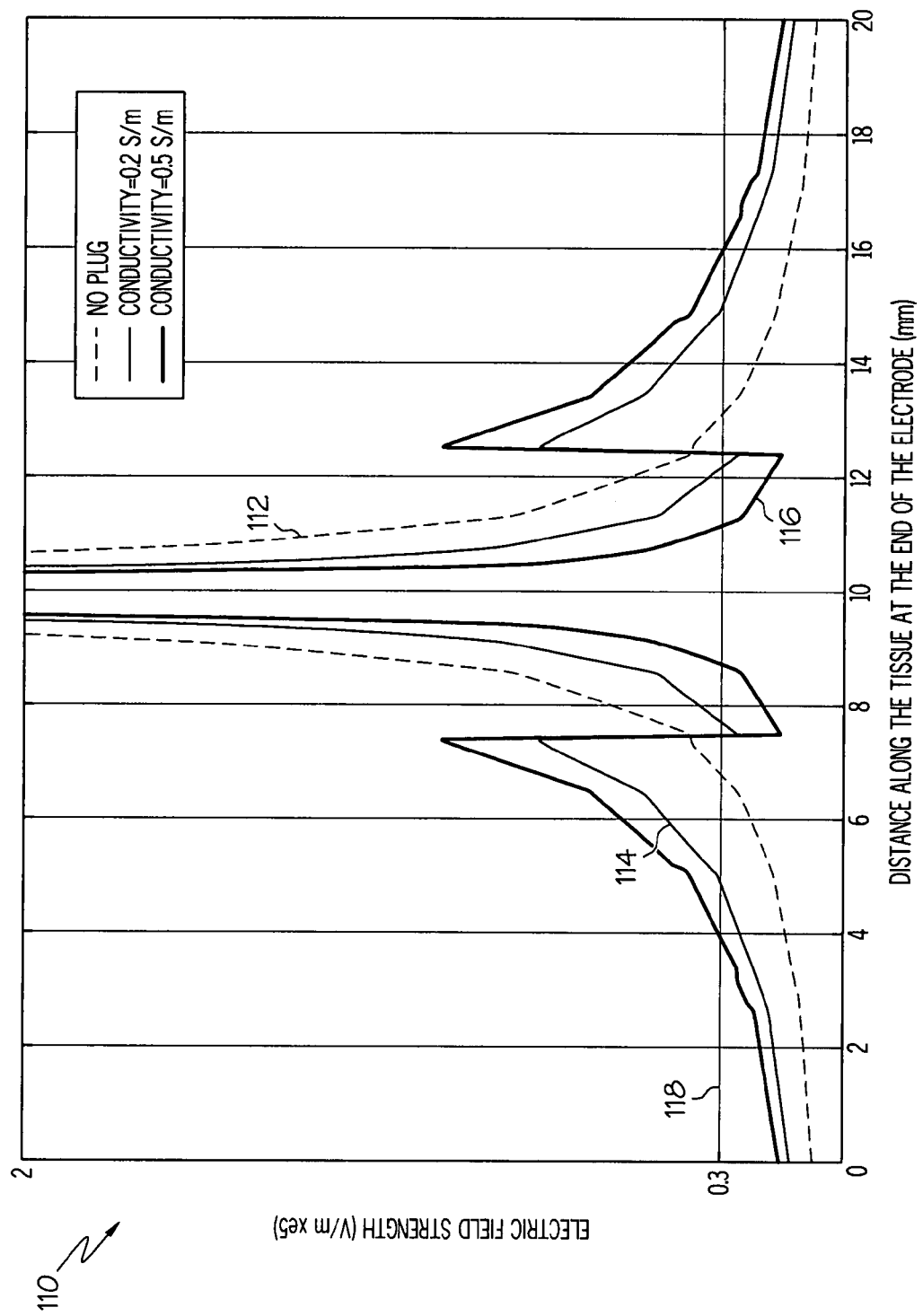
FIG. 15 is a close up of the graph shown in FIG. 14.

FIG. 14 is a graphical representation 110 (graph) of electric field strength (along the y-axis) as a function of distance from an electrical therapy electrode 28 under various conductivity environments near the diseased tissue 48. FIG. 15 is a close up of the graph 110 shown in FIG. 14A. In electrical therapy of diseased tissue 48, the volume of tissue that can be destroyed by an electrical waveform (e.g., the necrotic zone) may be defined by a minimum electric field strength applied to the tissue treatment region. The electric field strength in the tissue treatment region varies throughout the tissue as a function of the applied electrical waveform parameters frequency, amplitude, and pulse width as well as the conductivity of the tissue in the treatment region. When a single electrical therapy electrode 28 is located in a first position in the tissue treatment region of interest and a return pad is placed at a distance relatively far from the first position, an electric field is generated around the electrode 28 when it is energized with a particular electrical waveform. The magnitude of the electric field, however, diminishes rapidly in the radial direction away from the electrode 28. When two electrodes 28 are placed relatively close together, a larger pattern of tissue can be destroyed. Injecting a fluid having a higher conductivity than the tissue into the tissue treatment region extends the electric field of sufficient strength to destroy the tissue radially outwardly from the electrode 28. Thus, the addition of a fluid having higher conductivity than the tissue to be treated creates a larger tissue destruction zone by extending the electric field radially outwardly from the electrodes 28.

The graph 110 illustrates the electric field strength, along the y-axis, as a function of the radial distance from the electrical therapy electrode 28. The y-axis is labeled in units of volts/meter (V/m×e$^5$) and the x-axis is labeled in units of mm. The graph 110 illustrates a family of three functions with conductivity as a parameter. A first function 112 illustrates the electric field strength as a function of the radial distance from one of the electrodes 28 with no conductivity plug introduced into the tissue treatment region. A second function 114 illustrates the electric field strength as a function of the radial distance from one of the electrodes 28 with a conductivity plug of 0.2 S/m introduced in the tissue treatment region. A third function 116 illustrates the electric field strength as a function of the radial distance from one of the electrodes 28 with a conductivity plug of 0.5 S/m introduced in the tissue treatment region. As shown in the graph 110, the peak electric field strength of each of the functions 112, 114, 116 decreases with increased conductivity in the tissue treatment region in proximity to the electrode 28. However, the threshold 118 of each of the functions 112, 114, 116 where the electric field strength drops below the minimum threshold 118 of electric field strength required to destroy tissue becomes wider as the conductivity increases. In other words, increasing the conductivity of the tissue in the tissue treatment region extends the range of an effective electric field to destroy tissue or creates a larger necrotic zone. In one embodiment, the minimum electric field strength threshold 118 is approximately 30,000V/m.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the various embodiments of the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

It is preferred that the device is sterilized. This can be done by any number of ways known to those skilled in the art including beta or gamma radiation, ethylene oxide, steam.

Although the various embodiments of the invention have been described herein in connection with certain disclosed embodiments, many modifications and variations to those embodiments may be implemented. For example, different types of end effectors may be employed. Also, where materials are disclosed for certain components, other materials may be used. The foregoing description and following claims are intended to cover all such modification and variations.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

What is claimed is:

1. An ablation device, comprising:
    an elongate flexible member having a proximal end and a distal end and comprising:
    a first working channel formed within the flexible member;
    a first diagnostic probe having a proximal end and a distal end, the first diagnostic probe located within the first working channel and extending through the distal end of the flexible member; and
    a first electrode connected to the distal end of the first diagnostic probe;
    wherein the first electrode is adapted to be endoscopically located in a tissue treatment region; and
    wherein the first electrode is adapted to couple to an electrical waveform generator to receive an irreversible electroporation electrical waveform sufficient to ablate tissue located proximate to the first electrode;
    a second working channel formed within the flexible member;
    a second diagnostic probe having a proximal end and a distal end, the second diagnostic probe located within the second working channel and extending through the distal end of the flexible member; and
    a second electrode connected to the distal end of the second diagnostic probe;
    wherein the second electrode is adapted to be endoscopically located in a tissue treatment region;
    wherein the second electrode is adapted to couple to an electrical waveform generator to receive an irreversible electroporation electrical waveform sufficient to ablate tissue located between the first and second electrodes; and wherein the first and second electrodes are rotatable about a central axis defined through each of the first and second diagnostic probes, wherein a distance between the first and second electrodes is adjustable by rotating either one or both of the first and second diagnostic probes.

2. The ablation device of claim 1, wherein the first diagnostic probe comprises a sharp distal end and an aperture in communication with a bore formed within the first diagnostic probe to receive a tissue sample therethrough.

3. The ablation device of claim 1, wherein the second diagnostic probe comprises a sharp distal end and an aperture in communication with a bore formed within the second diagnostic probe to receive a tissue sample therethrough.

4. The ablation device of claim 1, comprising:
   at least one illuminator supported on the device and positioned to illuminate tissue; and
   an image sensor supported on the device and positioned to image tissue therethrough.

5. An ablation system, comprising:
   an ablation device comprising:
   an elongate flexible member having a proximal end and a distal end and comprising:
   a first working channel formed within the flexible member;
   a first diagnostic probe having a proximal end and a distal end, the first diagnostic probe located within the first working channel and extending through the distal end of the flexible member; and
   a first electrode connected to the distal end of the first diagnostic probe;
   wherein the first electrode is adapted to be endoscopically located in a tissue treatment region; and
   wherein the first electrode is adapted to receive an irreversible electroporation electrical (IRE) waveform sufficient to ablate tissue located proximate to the first electrode;
   a second working channel formed within the flexible member;
   a second diagnostic probe having a proximal end and a distal end, the second diagnostic probe located within the second working channel and extending through the distal end of the flexible member; and
   a second electrode connected to the distal end of the second diagnostic probe;
   wherein the second electrode is adapted to be endoscopically located in a tissue treatment region;
   wherein the second electrode is adapted to couple to an electrical waveform generator to receive an IRE waveform sufficient to ablate tissue located between the first and second electrodes; and
   wherein the first and second electrodes are rotatable about a central axis defined through each of the first and second diagnostic probes to adjust a distance between the first and second electrodes by rotating either one or both of the first and second diagnostic probes; and
   an electrical waveform generator electrically coupled to the first and second electrodes of the ablation device to generate an IRE waveform sufficient to ablate tissue located proximate to the first and second electrodes.

6. The ablation system of claim 5, wherein the first diagnostic probe comprises a sharp distal end and an aperture in communication with a bore formed within the first diagnostic probe to receive a tissue sample therethrough.

7. The ablation system of claim 5, wherein second diagnostic probe comprises a sharp distal end and an aperture in communication with a bore formed within the second diagnostic probe to receive a tissue sample therethrough.

8. The ablation system of claim 5, wherein the ablation device comprises at least one illuminator supported on the device and positioned to illuminate tissue; and an image sensor supported on the device and positioned to image tissue therethrough.

9. The ablation system of claim 8, wherein the electrical waveform generator is adapted to receive IRE electrical waveform parameters from an image processing module; wherein the IRE electrical waveform parameters are determined based on image information of the diseased tissue region in a patient.

10. The ablation system of claim 9, wherein the IRE electrical waveform parameters are determined based on a volume and outline of a necrotic zone required to treat the diseased tissue based on the image information.

11. The ablation system of claim 10, wherein the volume and outline of the necrotic zone are determined from geometric information extracted from the image information.

12. The ablation system of claim 9, wherein the IRE electrical waveform parameters comprise amplitude, frequency, and pulse width of an electrical waveform suitable to destroy the diseased tissue.

\* \* \* \* \*